United States Patent
Paul et al.

(10) Patent No.: US 6,791,011 B1
(45) Date of Patent: Sep. 14, 2004

(54) PROTEIN COMPLEMENTATION IN TRANSGENIC PLANTS

(75) Inventors: Wyatt Paul, Cambridgeshire (GB); Pascual Perez, Vareunes Chauorat (FR); Eric Huttner, Versailles (FR); Andreas Stefan Betzner, Canberra (AU)

(73) Assignee: Gene Shears Pty. Limited (AU)

( * ) Notice: Subject to any disclaimer, the term of this patent is extended or adjusted under 35 U.S.C. 154(b) by 0 days.

(21) Appl. No.: 09/377,502

(22) Filed: Aug. 20, 1999

Related U.S. Application Data

(63) Continuation of application No. PCT/GB98/00542, filed on Feb. 20, 1998.

(30) Foreign Application Priority Data

Feb. 21, 1997 (GB) .............................................. 9703681

(51) Int. Cl.⁷ ........................ C12N 15/82; C12N 15/55; C12N 15/62; A01H 1/02; A01H 5/00
(52) U.S. Cl. ....................... 800/287; 800/260; 800/271; 800/274; 800/278; 800/288; 800/290; 800/303; 435/69.7; 435/69.8; 435/199
(58) Field of Search ................................ 800/260, 271, 800/274, 278, 287, 288, 290, 303, 284; 435/69.7, 69.8, 199

(56) References Cited

U.S. PATENT DOCUMENTS

| | | | |
|---|---|---|---|
| 5,801,027 A | * | 9/1998 | Bennett et al. ............ 435/172.3 |
| 5,880,333 A | * | 3/1999 | Goff et al. ................... 800/288 |
| 6,392,119 B1 | | 5/2002 | Gutterson et al. ........... 800/278 |

FOREIGN PATENT DOCUMENTS

| | | | |
|---|---|---|---|
| EP | 938106549 | | 9/1993 |
| WO | 9109957 | | 7/1991 |
| WO | WO-93/17093 | * | 9/1993 |
| WO | 9520668 | | 8/1995 |
| WO | WO-96/00789 | * | 1/1996 |
| WO | 9604393 | | 2/1996 |
| WO | 9640950 | | 12/1996 |
| WO | 9740179 | | 10/1997 |
| WO | 9832325 | | 7/1998 |

OTHER PUBLICATIONS

Hiatt, A., Cafferkey, R., and Bowdish, K. (1989) "Production of Antibodies in Transgenic Plants," *Nature* 342:76–78.

Hiatt, A. and Ma, J.K–C. (1992) "Monoclonal Antibody Engineering in Plants," *FEBS* 307:71–75.

Sancho, J. and Fersht, A.R. (1992) "Dissection of an Enzyme by Protein Engineering," *J. Mol. Biol.* 224:741–747.

Lloyd, A.M., Walbot, V., and Davis, R.W. (1992) "Arabidopsis and Nicotiana Anthocyanin Production Activated by Maize Regulators R and Cl," *Science* 258:1773–1775.

Krizek, B.A. and Meyerowitz, E.M. (1996) "The Arabidopsis homeotic Genes APETALA3 and PISTILLALA are Sufficient to provide the B class Organ Identity Function," *Development* 122:11–22.

\* cited by examiner

Primary Examiner—David T. Fox
(74) Attorney, Agent, or Firm—John P. White; Cooper & Dunham LLP

(57) ABSTRACT

The invention relates to pairs of parent plants for producing hybrid seeds and to methods for producing plants with a desired phenotype. The desired phenotype is an active enzyme, a regulatory protein or a protein which affects the functionality and/or viability and/or structural integrity of a cell. Preferably, the desired phenotype is substantially absent from the parent plants/lines. In particular, the invention relates to parent plants and methods involving plant lines for producing male-sterile plants and seeds.

41 Claims, 15 Drawing Sheets

FIGURE 1A

Barnase coding sequence

Figure 2:
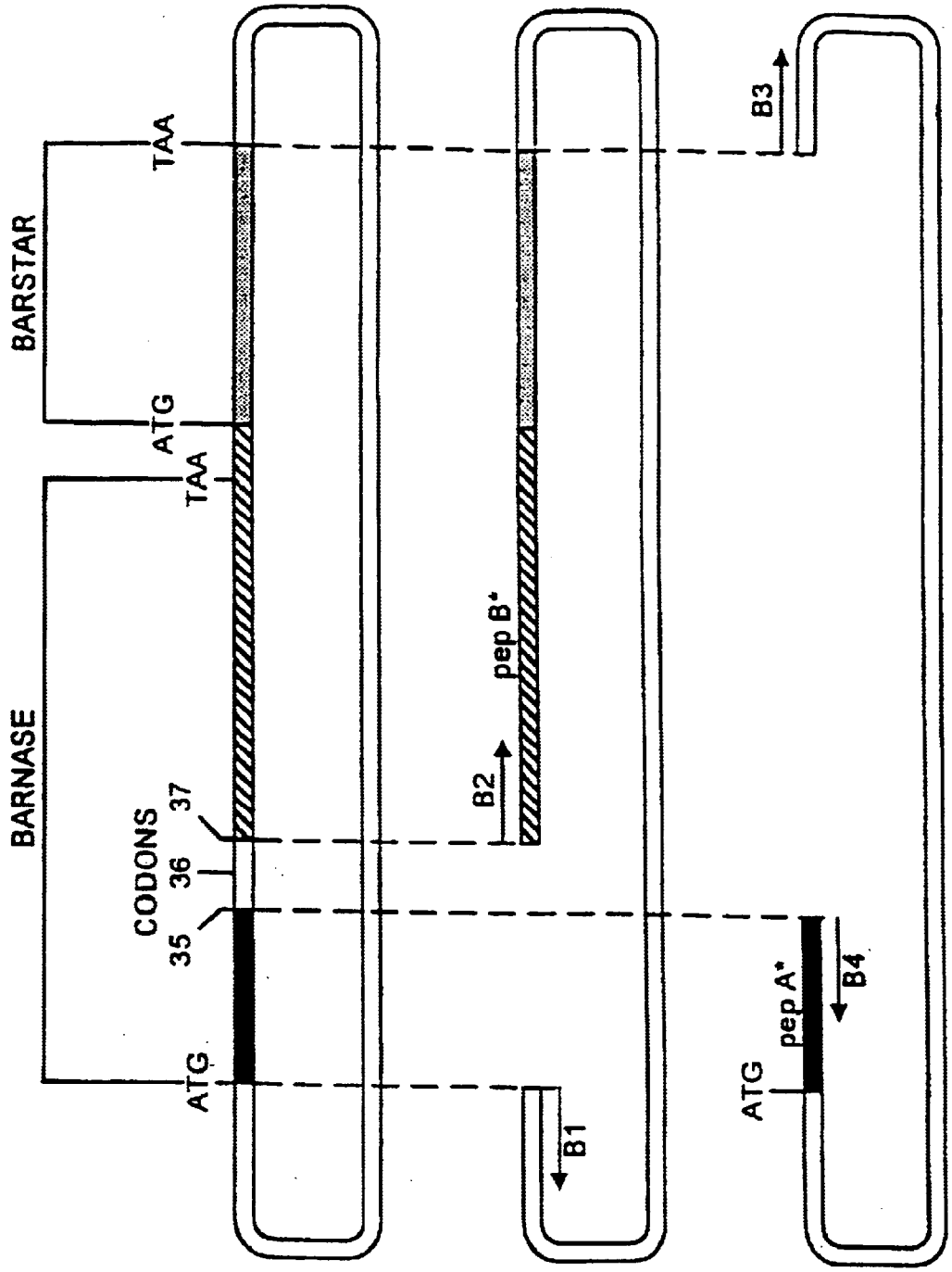

```
        met ala gln val ile asn thr phe asp gly val ala asp tyr leu gln thr tyr
TCTAGACC ATG GCA CAG GTT ATC AAC ACG TTT GAC GGG GTT GCG GAT TAT CTT CAG ACA TAT
3'gttccatgagatctgg tac 5' (B1 primer)

his lys leu pro asp asn tyr ile thr lys ser glu ala gln ala leu gly trp
CAT AAG CTA CCT GAT AAT TAC ATT ACA AAA TCA GAA GCA CAA GCC CTC GGC TGG
                                    (B4 primer) 3'  t gtt cgg gag ccg accS' val ala ser lys gly asn leu ala asp val ala pro gly lys ser ile gly gly
GTG GCA TCA AAA GGG AAC CTT GCA GAC GTC GCT CCG GGG AAA AGC ATC GGC GGA
5'gca tca aaa ggg aac c 3' (B2 primer)

asp ile phe ser asn arg glu gly lys leu pro gly lys ser gly arg thr trp
GAC ATC TTC TCA AAC AGG GAA GGC AAA CTC CCG GGC AAA AGC CGA ACA TCG arg glu ala asp ile asn tyr thr ser gly phe arg asn ser asp arg ile leu
CGT GAA GCG GAT ATT AAC TAT ACA TCA GGC TTC AGA AAT TCA GAC CGG ATT CTT tyr ser ser asp trp leu ile tyr lys thr thr asp his tyr gln thr phe thr
TAC TCA AGC GAC TGG CTG ATT TAC AAA ACA ACG GAC CAT TAT CAG ACC TTT ACA lys ile arg OCH
AAA ATC AGA taa
```

FIGURE 1B

Intergenic sequence

CGAAAAACGGCCTCCTGCGGAGGCCGTTTTTTCAGCTTTACATAAGTGTAATAAATTTTCTTCAAACTCTGATCGGTCAATTT
CACTTTCCGGATCCGGTCAATCTGAGCCGTCCGAGACAGGAGGACATCGTCCAGCTGAAACCGGGCAGAATCCGGCCATTTCTGAAG
AGAAAATGGTAAACTGATAGAATAAAATCATAAGAAGGAGCCGCAC

FIGURE 1C

Barstar coding sequence

```
    Met lys lys ala val ile asn gly glu gln ile arg ser ile ser asp leu his
1   ATG AAA AAA GCA GTC ATT AAC GGG GAA CAA ATC AGA AGT ATC AGC GAC CTC CAC gln thr leu lys lys glu leu ala leu pro glu tyr tyr gly glu asn leu asp
1   CAG ACA TTG AAA AAG GAG CTT GCC CTT CCG GAA TAC TAC GGT GAA AAC CTG GAC ala leu trp asp cys leu thr gly trp val glu tyr pro leu val leu glu trp
1   GCT TTA TGG GAT TGT CTG ACC GGA TGG GTG GAG TAC CCG CTC GTT TTG GAA TGG arg gln phe glu gln ser lys gln leu thr glu asn gly ala glu ser val leu
1   AGG CAG TTT GAA CAA AGC AAG CAG CTG ACT GAA AAT GGC GCC GAG AGT GTG CTT gln val phe arg glu ala lys ala glu gly cys asp ile thr ile ile leu ser
1   CAG GTT TTC CGT GAA GCG AAA GCG GAA GGC TGC GAC ATC ACC ATC ATA CTT TCT OCH
1   TAA TACGATCAATGGGAGATGAACAATATAGATCCCCCGGGCTGCAGGAATTC
    5' taa tacgatcaatgggagatg 3' (B3 primer)
```

1: Translation of DNA sequences encoding Barnase (A) and Barstar (C), respectively
2: DNA sequence encoding either Barnase (A), Barstar (C) or the synthetic intergenic region (B) according to Paul et al. (1992)
3: Sequence of DNA primers that were used for PCR to construct pepA* (B3/B4) and pepB* (B1/B2).

FIGURE 1D

Translational fusion of
ORF Peptide A**/(Gly4 ser) 3 Linker peptide / GUS

```
                met ala gln val ile asn thr phe asn gly val ala asn tyr leu gln thr tyr his lys
tctagacc        ATG GCA CAG GTT ATC AAC ACG TTT GAC GGG GTT GCG GAT TAT CTT CAG ACA TAT CAT AAG leu pro asn asp tyr ile thr lys ser glu ala gln ala leu gly trp met gly gly
CTA CCT GAT AAT TAC ATT ACA AAA TCA GAA GCA CAA GCC CTC GGC TGG ATG GGC GGT GGC gly ser gly gly gly ser gly gly gly ser gly ile pro gly tyr gly gln ser
GGT TCC GGT GGC AGC GGT GGC GGT AGC GGg atc ccc ggg tac ggt cag tcc pro met
ctt atg ... of GUS
```

Underlined: ORF of peptide A**

FIGURE 1E

Nucleotide Sequence of Translational fusion of
Ubiquitin genomic sequence and ORF Peptide A***

```
tctagacc ATGCAGATCT TCGTGAAAAC CTTGACCGGC AAGACCATCA CTCTCGAGGT CGAGAGCAGC CACACCATCG
ACAATGTCAA GGCCAAGATC CAAGACAAAG AAGGTATCAT TCTTCCTCAC TCTTCTCTT TAGTTTTG
AATTCAGAT CTCTTATCAT TTACTGTTT CTCCTTTAAG GATCAGCAG AGATTGATCT TCGCCCGAAA
GCAGCTCGAA GATGGCCGTA CTTTGGCTGA CTACAACATC CAGAAAGGTA CGAATCATC CGAATCCTTC TGTTGATCAT
TTCGATGATC TGATTGTATA ACTCTAAATG GATTGTTATC AGAATCTACA CTTCATCTTG TGTTGACGCT
TAGCCTGGA GCACAGGTTA TCAACACGTT TGACGGGGTT GCGGATTATC TTCAGACATA TCATAAGCTA CCTGATAATT
ACATTACAAA ATCAGAAGCA CAAGCCCTCG GCTGGATGTA Gggatcc
```

Underlined: Introns A and B within the ubiquitin sequence.
Bold: glycine codon 76 at the end of the ubiquitin ORF

FIGURE 1F

Nucleotide Sequence of Translational fusion of
Ubiquitin genomic sequence and ORF Peptide B***

```
tctagacc ATGCAGATCT TCGTGAAAC  CTTGACCGGC AAGACCATCA CTCTCGAGGT CCAGAGCAGC GACACCATCC
ACAATGTCAA GGCCAAGATC CAAGACAAAG AAGTATCAT  TCTTCCTCAC TCAATCTGGA TCTTCTCTT  TAGCTTTTG
AATTCAGAT  CCTTATCAT  TACTTGTTT  CTCCTTAAG  GAATCCCTCC GGATCAGCAG AGATTGATCT TCGCCCGAAA
GCAGCTCGAA GATGCCCGTA CTTGGCTGA  CTACAACATC CAGAAAGTA  CGAAATCATC GGAATCCTTC TGTTGATCAT
TTCGATGATC TGTTGTATA  AACTCTAAAG AATGGTATC  GAATGTAAAC AGAATCTACA CTTCATCTTG TGTTGAGGCT
TAGAGTGGA  GCATCAAAAG CGAACCTTGC AGACGTCGCT CCGGGGAAAA GCATCGGGGG AGACATCTTC TCAAACAGGG
AAGGCAAACT CCCGGGCAAA AGCGGACGAA CATGGCGTGA AGCGGATATT AACTATACAT CAGGCTTCAG AAATTCAGAC
CGGATTCTTT ACTCAAGCGA CTGGCTGATT TACAAACAA  CGGACCATTA TCAGACCTTT ACAAAATCA  GATAA...
```

Underlined: Introns A and B within the ubiquitin sequence.
Bold: glycine codon 76 at the end of the ubiquitin ORF

FIGURE 1G

DNA sequence of T PCR primers (example 1)

| | | |
|---|---|---|
| B5 | 5' CACAAGTACTCTAGACCATG 3' | (forward) |
| B6 | 5' CATCCAGCCGAGGGCTTGT 3' | (reverse) |
| B7 | 5' GGCGGTGGCCGTTCCG 3' | (forward) |
| B8 | 5' CCACTAGTTCTAGAGTACTTGTG 3' | (reverse) |
| B9 | 5' GCACAGGTTATCAACACG 3' | (forward) |
| B10 | 5' GCGGATCCTCTACATCCAGCCCGAGGGCTTGT 3' | (reverse) |
| B11 | 5' GCATCAAAAGGGAACC 3' | (forward) |
| B12 | 5' GGTCTAGAGTACTTGTG 3' | (reverse) |
| Ubq16F | 5' GCTCTAGACCATGCAGATCTTCGTGAAAAC 3' | (forward) |
| Ubq1R | 5' CTGGATCCACCTCTAAGCCTCAACA 3' | (reverse) |
| Ubq1a | 5' TATGGATCCCCGGCTGCAGGAA 3' | (forward) |
| Ubq1b | 5' TCCACCTCTAAGCCTCAACAC 3' | (reverse) |

FIGURE 3A

In Vitro Construction from Synthetic Obligonucleotides of S-peptide, S(+5)-protein and S-protein

```
1.  5'-gcggatccatgaaggagaccgcc-3OH
2.  5'-gcggatccatgaaggagaccgccgcccgccaagttcgagcgccagcacatgacagc-3OH     5P-TAAAGATCTATG...
3.                                                   3OH-GTACCTGTCG          ATTTCTAGATAC-5'

4.  5'-ccagatctATG-----AGCTCCTCCAACTACTG-3OH
5.  ...AGCACCTCCGCCCCGCCAGTCCTCCAACTACTGCAACCAGATGATGAAGTCT-3OH        5P-AGGAACCTTGA...
6.                                                   3OH-ACTACTTCAGA          TCCTTGGACT-5'

7.  ...CCAAGGAGACAGGTGCAAGCCAGTCAACACCTTCGTCCACGAGAGCCTGGC-3OH         5P-CGATGTCCAG...
8.                                                   3OH-CTCGGACCG            GCTACAGGTC-5'

9.  ...GCCGTCTGCAGCCAGAAGAACGTGGCCTGCAAGAACGG-3OH                     5P-TCAGACCAACT...
10.                                                   3OH-CGTTCTTGCC          AGTCTGGTTGA-5'

11. ...GCTACCAGTCCTACAGCACCATGTCCATCACCGACTGCCGGGAGACCGG-3OH           5P-CTCCAGCAAG...
12.                                                   3OH-GCTCTGGCC            GAGGTCGTTC-5'

13. ...TACCCTAACTGCGCCTACAAGACCACCCAGGCCAACAAGCACATC-3OH               5P-ATTGTTGCCTG...
14.                                                   3OH-GTTCGTGTAG            TAACAACGGAC-5'

15.                                                   3OH-CTGCGGAGGCAGATTtcctagggc-5'
16. ...CGAGGGTAACCCTTACGTGCCTGTCCACTTCGACGCCTCGTCTAAaggatcccg-3OH
```

FIGURE 3B

In Vitro Construction from Synthetic Obligonucleotides
of the Sequence encoding the S-peptide and the (Gly4-Ser)3 Linker 1. 5'-gcggatccCATGAAGGAGACCGCC-3OH
2. 5'-gcggatccCATGAAGGAGACCGCCCCGCCCGGCCAAGTTCGAGGCCAGCACATGGACAGC-3OH
3. 3OH-GTACCTGTCG                                                       5P-GGCGGTGG...:
4. ...CGGTTCCGGTGGCGGTGGCAGCGGCGGTGGTGGTAGCaagatcttcggg-3OH                CCGCCACC-5';
5.                                       3OH-CCATCGttctagaagccc-5'

FIGURE 4A

Protein and DNA Sequences of S-peptide and S-peptide with (Gly-4 Ser) 3 Linker

```
1  ---  ---  AAA  GAG  ACA  GCA  GCC  GCA  AAG  TTT  GAG  CGT  CAG  CAT  ATG  GAT  AGT  ---  ---  ---  ---  ---  ---
2  ---  MET  lys  glu  thr  ala  ala  ala  lys  phe  glu  arg  gln  his  met  asp  ser  ---  ---  ---  ---  ---  ---
3  ggatcc  atg  aag  GAG  acc  gcc  GCC  gcc  AAG  ttc  GAG  cgc  CAG  cac  ATG  gac  agc  ocn  ---  gly  gly  gly  ---
4  ggatcc  atg  aag  GAG  acc  gcc  GCC  gcc  AAG  ttc  GAG  cgc  CAG  cac  ATG  gac  agc  taa  ---  ggc  ggc  ggc  ggt 1  ---  ---  ---  ---  ---  ---  ---  ---  ---  ---  ---  ---
2  gly  gly  gly  ser  gly  gly  gly  gly  ser  ---  ---  ---
3  ---  ---  ---  ---  ---  ---  ---  ---  ---  ---  -agatct
4  ggt  ggc  ggc  agc  ggc  ggt  ggt  ggt  agc  agc  aagatct
```

Legend to Figure 4A:

1: DNA sequence of the synthetic Bovine Rnase A gene (codon 1 to 15) according to N. Vasantha and David Filpula (1989)
2: Translation of synthetic DNA sequences encoding Bovine RNase A
3: DNA sequence of the S-peptide coding sequence referred to in this invention
4: DNA sequence encoding the S-peptide with (gly4 ser)3 linker peptide referred to in this invention

FIGURE 4B

Protein and DNA Sequences of S(+5)-protein and S-protein

```
        ---  AGC ACC AGT GCT GCC AGT TCT TCC AAC TAC TGT AAC CAG ATG ATG AAG TCT ACA AAC TTG ACC AAG
1       met  ser thr ser ala ala ser ser ser asn tyr cys asn gln met met lys ser arg asn leu thr lys
2 agatct atg AGC ACC --- --- GCC AGC TCC AAC TAC TAC AAC CAG ATG ATG AAG TCT AGG AAC CTG ACC AAG
3 agatct atg --- --- --- --- --- --- --- --- --- --- --- --- --- --- --- --- --- --- --- --- ---
4 agatct atg --- --- --- --- gcc agc tcc aac tac tgc aac cag atg atg aag tct agg aac ctg acc aag GAC AGA TGT AAG CCA GTT AAC ACA TTT GTC CAC GAG AGT TTG GCT GAT GTC CAA GCC GTC TGC AGT
1   asp arg cys lys pro val asn thr phe val his glu ser leu ala asp val gln ala val cys ser
2   GAC AGG TGC AAG CCA GTC AAC ACC TTC GTC CAC GAG AGC CTG GCC GAC GTC CAG GCC GTC TGC AGC
3   --- --- --- --- --- --- --- --- --- --- --- --- --- --- --- --- --- --- --- --- --- ---
4   GAC AGG TGC AAG CCA GTC AAC ACC TTC GTC CAC GAG AGC CTG GCC GAC GTC CAG GCC GTC TGC AGC CAG AAA AAC GTT GCA TGC AAG AAC GGT CAA ACG AAC TGT TAC CAG AGT TAC AGC ACC ATG TCC ATC
1   gln lys asn val ala cys lys asn gly gln thr asn cys tyr gln ser tyr ser thr met ser ile
2   CAG AAG AAC GTG GCC TGC AAG AAC GGT CAG ACC AAC TGC TAC CAG AGC TAC TCC ACC ATG TCC ATC
3   CAG AAG AAC GTG GCC TGC AAG AAC GGT CAG ACC AAC TGC TAC CAG AGC TAC TCC ACC ATG TCC ATC
4   CAG AAG AAC GTG GCC TGC AAG AAC GGT CAG ACC AAC TGC TAC CAG AGC TAC TCC ACC ATG TCC ATC ACT GAC TGT CGT GAG ACA GGC TCG AGC AAG AAG TAT CCT AAT TGT GCT TAC AAG ACC ACA CAG GCG AAC
1   thr asp cys arg glu thr gly ser ser lys lys tyr pro asn cys ala tyr lys thr thr gln ala asn
2   ACC GAC TGC CGC GAG ACC GGC AGC TCC AAG TAC CCC AAC TGC GCC TAC AAG ACC ACC CAG GCC AAC
3   ACC GAC TGC CGC GAG ACC GGC AGC TCC AAG TAC CCC AAC TGC GCC TAC AAG ACC ACC CAG GCC AAC
4   ACC GAC TGC CGC GAG ACC GGC AGC TCC AAG TAC CCC AAC TGC GCC TAC AAG ACC ACC CAG GCC AAC AAA CAC ATC ATT ATT GCT TGT GAA GGT AAC CCT TAC GTC CCT GTC CAC TTT GAC GCC AGT GTT TAA
1   lys his ile ile ile ala cys glu gly asn pro tyr val pro val his phe asp ala ser val och
2   AAG CAC ATC ATC GTT GCC TGC GAG GGT AAC CCT TAC GTG CCT GTC CAC TTC GAC GCC TCC GCC TAA
3   AAG CAC ATC ATC GTT GCC TGC GAG GGT AAC CCT TAC GTG CCT GTC CAC TTC GAC GCC TCC GCC TAA
4   aag cac atc atc gtt gcc tgc gag ggt aac cct tac gtg cct gtc cac ttc gac gcc tcc gcc taa 1   ------
2   ------
3   aggatcc
4   aggatcc
```

Legend to Figure 4B:

1: DNA sequence of the synthetic Rnase A gene (codons 16 to 124) according to Vasantha and Filpula (1989)
2: Translation of DNA sequences encoding the Bovine RNase A
3: DNA sequence of the synthetic S(+5)-protein coding sequence (aa16 to aa124)
4: DNA sequence of the synthetic S-protein coding sequence (aa21 to aa124)

FIGURE 4C i. PCR amplification product encoding impartial AOX3 targeting signal

```
XbaI / BglII
tctagatcttaac ATGAAGAATG TTTTAGTAAG GTCAGCTGCG CGAGCTCTGC TTGGCGGCGG
              TGGGCGGAGC TACTACCGCC AGCTCTCAAC GGCGGCGATC GTGGAACAGA
              GACACCAGCA CGGTGGCGGC GCGTTTGGAA GCTTCCA cttaagcggatcc
                                                       AflII / BamHI
``` ii. ORF encoding AOX3 targeting sequence (underlined) and S-peptide

<u>ATGAAGAATG TTTTAGTAAG GTCAGCTGCG CGAGCTCTGC TTGGCGGCGG TGGGCGGAGC
TACTACCGCC AGCTCTCAAC GGCGGCGATC GTGGAACAGA GACACCAGCA CGGTGGCGGC
GCGTTTGGAA GCTTCCACTT</u> AAGAAGGATG AAGGAGACCG CCGCCGCCAA GTTCGAGCGC
CAGCACATGG ACAGCTAA iii. ORF encoding AOX3 targeting sequence (underlined) and S-peptide-(Gly4 Ser)3-GUS

<u>ATGAAGAATG TTTTAGTAAG GTCAGCTGCG CGAGCTCTGC TTGGCGGCGG TGGGCGGAGC
TACTACCGCC AGCTCTCAAC GGCGGCGATC GTGGAACAGA GACACCAGCA CGGTGGCGGC
GCGTTTGGAA GCTTCCACTT</u> AAGAAGGATG AAGGAGACCG CCGCCGCCAA GTTCGAGCGC
CAGCACATGG ACAGCGGCGG TGGCGGTTCC GGTGGCGGTG GCAGCGGCGG CGGTGGTAGC
GGGATCCCCG GGTACGGTCA GTCCCTTATG --> GUS iv. ORF encoding AOX3 targeting sequence (underlined) and S-protein

<u>ATGAAGAATG TTTTAGTAAG GTCAGCTGCG CGAGCTCTGC TTGGCGGCGG TGGGCGGAGC
TACTACCGCC AGCTCTCAAC GGCGGCGATC GTGGAACAGA GACACCAGCA CGGTGGCGGC
GCGTTTGGAA GCTTCCACTT</u> AAGAAGGATG AGCTCCTCCA ACTACTGCAA CCAGATGATG
AAGTCTAGGA ACCTGACCAA CGACAGGTGC AAGCCAGTCA ACACCTCCGT CCACGAGAGC
CTGGCCGATG TCCAGGCCGT CTGCAGCCAG AAGAACGTGG CCTGCAAGAA CGGTCAGACC
AACTGCTACC AGTCCTACAG CACCATGTCC ATCACCGACT GCCGCGAGAC CGGCTCCAGC
AAGTACCCTA ACTGCGCCTA CAAGACCACA CAGGCCAACA AGCACATCAT TGTTGCCTGC
GAGGGTAACC CTTACGTGCC TGTCCACTTC GACGCCTCCG TCTAA v. Translational fusion of Ubiquitin genomic sequence and ORF of S-protein

ATGCAGATCT TCGTGAAAAC CTTGACCGGC AAGACCATCA CTCTCGAGGT CGAGAGCAGC
GACACCATCG ACAATGTCAA GGCCAAGATC CAAGACAAAG AA<u>GGTATCAT TCTTCCTCAC
TCAATCTGGA TTCTTCTCTT TAGCTTTTTG AAATTCAGAT CTCTTATCAT TTACTTGTTT
CTCCTTAAG</u> GAATCCCTCC GGATCAGCAG AGATTGATCT TCGCCGGAAA GCAGCTCGAA
GATGGCCGTA CTTTGGCTGA CTACAACATC CAGAAA<u>GTA CGAAATCATC CGAATCCTTC
TGTTGATCAT TTCGATGATC TGATTGTATA AACTCTAATG GATTGTTATC ATTTGTAAAC
AGAATCTACA CTTCATCTTG TGTTGAGGCT TAGAGG</u>tGGa tcCagCTCCA ACTACTGCAA
CCAGATGATG AAGTCTAGGA ACCTGACCAA GGACAGGTGC AAGCCAGTCA ACACCTCCGT
CCACGAGAGC CTGGCCGATG TCCAGGCCGT CTGCAGCCAG AAGAACGTGG CCTGCAAGAA
CGGTCAGACC AACTGCTACC AGTCCTACAG CACCATGTCC ATCACCGACT GCCGCGAGAC
CGGCTCCAGC AAGTACCCTA ACTGCGCCTA CAAGACCACA CAGGCCAACA AGCACATCAT
TGTTGCCTGC GAGGGTAACC CTTACGTGCC TGTCCACTTC GACGCCTCCG TCTAA

Underlined: introns A and B within the ubiquitin encoding sequence
Bold: codon for Glycine[76], marking the C-terminus of the ubiquitin.
Small letters: PCR introduced conservative codon changes to generate a BamHI site and to modify the codon usage

FIGURE 4D

Nucleotide sequence of PCR primers (example3)

| | | |
|---|---|---|
| Sprot F | 5' | GGTGGATCCAGCTCCAACTACTGCAAC 3' |
| Sprot R | 5' | CGGGATCCTTAGACGGAGGGGTCG 3' |
| SprotMI1 | 5' | GTCCTTAAGAAGGATGAGCTCCTCCAACTAC 3' |
| SprotMI2 | 5' | CGGGATCCTTAGACGGAGGGGTCG 3' |
| SpepMI1 | 5' | GTCCTTAAGAAGGATGAAGGAGACCGCCG 3' |
| SpepMI2 | 5' | TCGGGATCCTTAGCTGTGTCCATGTGCTG 3' |
| SpepGMI2 | 5' | TCGGGATCCTCATTGTTTGCCTCCCTG 3' |
| AOX3MI1 | 5' | TGCTCTAGATCTTAACATGAAGAATGTTTAG 3' |
| AOX3MI2 | 5' | TCGGATCCGCTTAAGTTGGAAGCTTCCAAAC 3' |

FIGURE 5
*FIGURE SHOWING A PRODUCTION SCHEME OF EMBRYO LESS MAIZE GRAINS: LINES A AND B ARE SHOWN IN ALTERNATIVE ROWS (FOR EXAMPLE ONE MALE AND FOUR FEMALES)*
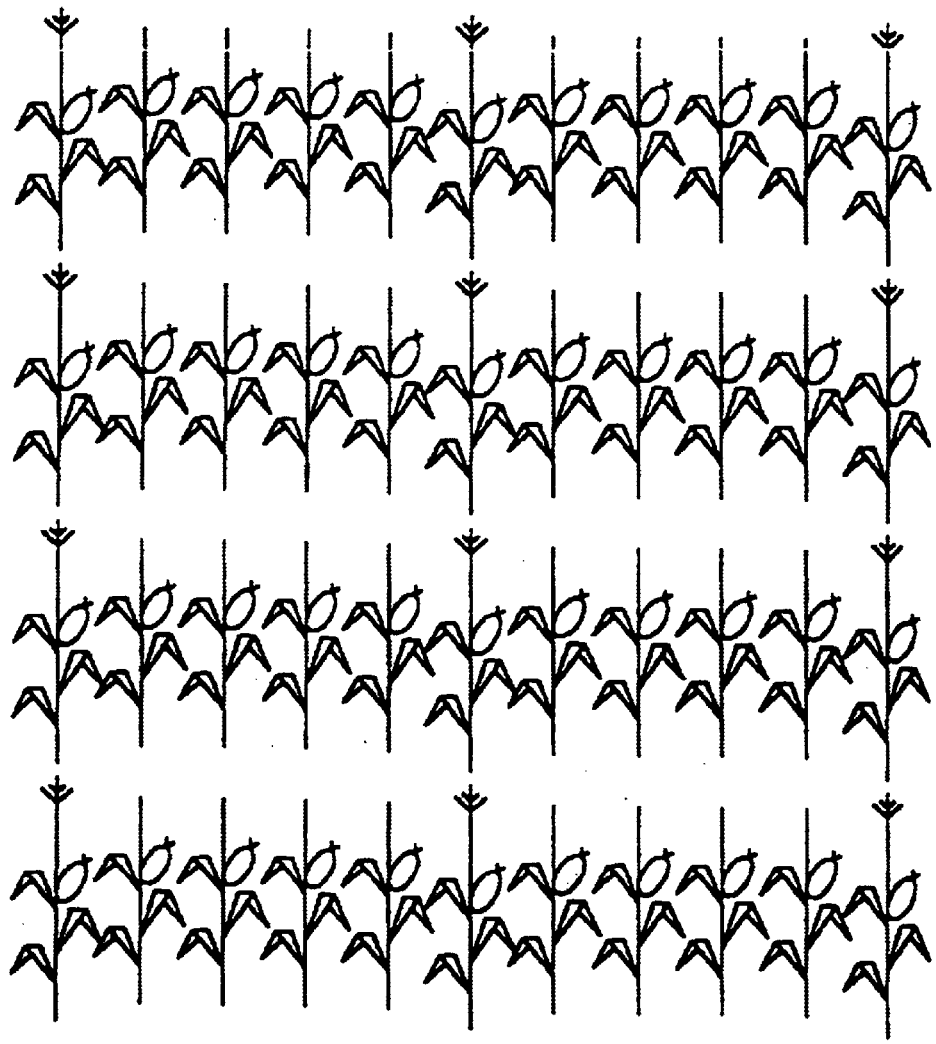
LEGEND
(REFER TO DESCRIPTION FOR DETAILS)
MALE PARENT A
FEMALE PARENT B

PROTEIN COMPLEMENTATION IN TRANSGENIC PLANTS

This application is a continuation of PCT International Application No. PCT/GB98/00542, filed Feb. 20, 1998, designating the United States of America, which is a claiming priority of British Patent Application No. 9703681.8, filed Feb. 21, 1997, the contents of which are hereby incorporated by reference into the present application.

This invention relates to pairs of parent plants for producing hybrid seeds and to methods for producing plants with a desired phenotype. The desired phenotype is an active enzyme, a regulatory protein or a protein which affects the functionality and/or viability and/or structural integrity of a cell. Preferably, the desired phenotype is substantially absent from the parent plants/lines. In particular, the invention relates to parent plants and methods involving plant lines for producing male-sterile plants and seeds.

The present invention describes a protein complementation system, with a variety of different applications. The system can be explained and exemplified with reference to obtaining male-sterile plants and embryoless seeds although it is not limited to these applications.

The use of dominant Artificial Male Sterility (AMS) in plants is described in WO95/20668. This document describes a binary system using two genes which together (but not in isolation) cause male sterility. The genes are brought together by crossing plants, each parent being homozygous for the gene, which generates a homogenous population of male sterile plants. WO95/20668 describes several ways to implement the gene binary system, including the following:

i. a system based on activation of transcription: a transcriptionally inactive AMS gene is activated upon crossing by provision of the relevant transcription factor;

ii. a system based on activation of splicing: an AMS gene inactivated by the presence of an intron is activated upon crossing by provision of the relevant maturase;

iii. a system based on the suppression of a stop codon during translation: an AMS gene inactivated by introducing an artificial stop codon in the ORF, is activated upon crossing by provision of an artificial stop suppressor tRNA for the introduced stop codon.

iv. a system based on sequence-specific gene inactivation: One parent contains a modified male fertility gene and a transgene which inactivates only the unmodified male fertility gene. The other parent contains a transgene which inactivates only the modified male fertility gene. In the hybrid both the modified and unmodified male fertility genes are inactivated causing male sterility.

v. a system based on preventing restoration of male fertility by a restorer gene: the first parent contains the AMS gene and the restorer gene, and the second parent contains a gene inhibiting the action of the restorer gene.

However, the binary systems described above have so far proved complex to implement and have encountered a variety of difficulties.

For example, it has been found that the use of a suppressor tRNA (described in Betzner et al. 1996, Abstract of the 14th International Congress of Plant Reproduction, Lorne, Australia) can have deleterious consequences for some plant species. While this does not preclude its use, it does make the screening of suitable transgenic plants more labour intensive than desirable. Another example is the leakiness of the T7 promoter (described in EP-A-0589841). Some plants transformed with a T7 promoter driving Barnase were sterile in the absence of the T7 RNA polymerase. Again, this does not preclude use of the system but it does make it difficult to identify suitable transgenic plants. Furthermore, in certain plants the gene binary system is sub-optimal since not all of the required genetic elements are fully characterised.

Two areas of prior art have been explored which have resulted in a phenotype conferred to a plant by the combination of two proteins.

In 1989, Hiatt and coworkers (Nature, vol. 342, p. 76–78) described the production of a functional antibody in tobacco by crossing tobacco plants expressing a gamma immunoglobulin gene and a kappa immunoglobulin gene.

Problems were, however, encountered with this system. Since the light and heavy chains of an antibody interact through disulfide bridges, the bridges were unable to form in the reducing environment present in the cytoplasm. Assembly of a functional antibody in plants thus requires that both chains are targeted to the endoplasmic reticulum then secreted to the apoplast (the space between cells). The production of antibodies in plants has thus been limited to the production of secreted antibodies or the production of single chain antibodies.

In 1992 Lloyd et al. (Science, vol. 258, p. 1773–1775) described the transfer in Arabidopsis and tobacco of two maize genes coding for the transcription factors R and C1. Ectopic expression of these genes separately in heterologous plants has some effect on the transcription of endogenous genes. In particular the genes have some effect in isolation, and this may preclude their use for applied purposes. Co-expression of the two genes had more dramatic qualitative and quantitative effects, than expression of either gene alone. However, these genes have properties severely limiting their usefulness and their general inapplication is described in the paper.

It has been shown that the Arabidopsis transcription factors Apetala3 and Pistillata can be ectopically co-expressed, and jointly in concert cause a new phenotype in the Arabidopsis flower (Krizek and Meyerowitz, 1996, Development, vol. 122, p. 11–22). The limitations described above for the R/C1 proteins also apply in this case.

The present invention describes a protein complementation system which overcomes many of the problems and difficulties associated with known gene binary systems. The protein complementation system according to this invention is based on the expression of two or more gene sequences in a single plant, which polypeptides/proteins, associate, interact or come together to form an active enzyme, a regulatory protein or a protein which affects the functionality and/or viability and/or the structural integrity of a cell. Hereinafter, in this text all references to a protein which affects the structural integrity of a cell also describes a protein which may, in addition, or alternatively, affect the functionality and/or viability of a cell. Some polypeptides/proteins may fall in more than one of these categories None of the individual gene sequences present in a given plant lead to a significant phenotypic effect in these plants.

The present invention describes the creation of a plant which has a desired phenotype through expression of an active enzyme, regulatory protein or protein which affects the structural integrity or a cell (eg. a membrane destabilizing protein) The plant may be obtained by crossing a pair of parent plants a and b. Plant a contains one or more gene sequences which encode a polypeptide(s) or protein(s) (A) with little or no activity so that the desired phenotype is not significantly (or substantially) caused by expression of the one or more genes in plant a alone. Plant b also contains one or more gene sequences which encode a polypeptide(s) or protein(s) (B) also, with little or no activity so that the desired phenotype is not significantly (or substantially) caused by expression of the one or more genes in plant b alone. When plants a and b are crossed, the resulting hybrid expresses both polypeptides and/or proteins A and B. These two polypeptides/proteins associate, interact or come together to form an active enzyme, regulatory protein or protein which affects the structural integrity of the cell, with the result that the daughter plant displays the desired phenotype. NB: From hereon, when discussing the polypeptides/proteins A or B they will be referred to only as 'polypeptides' for the sake of convenience.

This protein complementation binary system is simpler than the previously described binary systems since there is no need for interaction between genes, no required modification of the expression of genes and no modification of the level of expressed polypeptides in the daughter plant compared to the parent plants.

The present invention is described with reference to the Figures which are:

FIG. 1A; Barnase coding sequence;

FIG. 1B; Intergenic sequence;

FIG. 1C; Barstar coding sequence;

FIG. 1D; Translational fusion of ORF Peotide A**/(Gly4 ser)3 Linker peptide/GUS;

FIG. 1E; Nucleotide sequence of Translational fusion of Ubiquitin genomic sequence and ORF Peptide A***;

FIG. 1F; Nucleotide sequence of Translational fusion of Ubiquitin genomic sequence and ORF peptide B***

FIG. 1G; DNA sequence of IPCR (inverse polymerase chain reaction) primers (example 1)

FIG. 2; Schematic illustration of pepA* and pepB* construction by: Inverse PCR (IPCR)

FIG. 3A; In vitro construction from synthetic oligonucleotides of S-peptide, S(+5)-protein and S-protein;

FIG. 3B; In vitro construction from synthetic oligonucleotides of the sequence encoding the S-peptide and the (Gly4-Ser)3 linker;

FIG. 4A; protein and DNA sequences of S-peptide and S-peptide with (Gly4-Ser)3 linker;

FIG. 4B; protein and DNA sequences of S(+5)-protein and S-protein.

FIG. 4C(i); PCR amplification product encoding partial AOX3 targeting signal;

(ii); ORF encoding AOX3 targeting sequence (underlined) and S-peptide (iii); ORF encoding AOX3 targeting sequence (underlined) and S-peptide/(Gly4 Ser)3/GUS (iv); ORF encoding AOX3 targeting sequence (underlined) and S-protein (v); translational fusion of Ubiquitin genomic sequence and ORF of S-protein;

FIG. 4D; nucleotide sequence of IPCR primers (example 3)

FIG. 5; production scheme for embryoless maize grains.

Embryoless seeds harvested from female rows only= 100% of embryoless maize seeds or Seeds harvested from all the field plants=approximately 80% of embryoless maize seeds:

note that if this sort of seeds harvesting is suited a random sowing with 10% of male plants and 90% of female plants is desirable and possible.

Legend male parent A expressing pepA* in embryos

Genotype: emb-pepA*/emb-pepA* or emb-pepA* linked to Herbicide resistance/emb-pepA* linked to herbicide resistance female parent B expressing pepB* in embryos only Genotype: emb-pep*/emb-pepB* in a male sterile cytoplasmic environment or emb-pepB*/emb-pepB*

Artificial Male Sterility linked to Herbicide Resistance/+

According to a first aspect of the invention there is provided a pair of parent plants for producing seeds comprising:

(i) a first parent plant containing one or more gene sequences encoding a polypeptide A; and (ii) a second parent plant containing one or more gene sequences encoding a polypeptide B;

wherein the polypeptides A, B, when expressed separately in different plants, do not form an active enzyme a regulatory protein or other protein which affects the structural integrity of the cell but when expressed in the same plant do form an active enzyme, regulatory protein or other protein which affects the structural integrity of the cell. Presence of the active enzyme, regulatory protein or protein which affects the structural integrity of the cell in a single plant, is the desired phenotype.

The present invention includes the scenario of inter-extragenic repression/complementation/suppression; that is, where a mutation in one subunit of a multi-subunit complex can complement a mutation in another sub-unit in order to restore the active enzyme, regulatory protein or protein affecting the structural integrity of the cell. In such a scenario, the polypeptide(s)/protein(s) A and B may be the same in the two parent plants, with the exception of the different mutations. Examples include the *E.coli* regulatory proteins as described by Tokishita S. I., and Mizuno T., 1994, *Mol. Microbiol.* (UK), 13/3, 435–444 and the GroES and GroEL proteins of *E.coli* as described by Zeilstra-Ryalls J., et al., 1994, *J. Bacteriol.* (US), 176, (21), 6558–65.

In the present invention, the pair of parent plants can be described as a pair of complementary plants for producing hybrid seeds or even a pair of complementary transgenic plants for producing transgenic hybrid seeds.

It is most likely that at least one of the pair of parent plants is transgenic. When used herein the term 'transgenic' refers not only to genetic material from another species but to genetically manipulated DNA Prom the same plant or species. The genetic manipulation of the plant may be by a microbiological process such as *Agrobacterium tumefaciens* (Horsch R. B., Fry J. E., Hoffman N. L., Eichholtz D., Rogers S. G., Fraley R. T., (1985), Science, 227: 1229–1231)). Alternative manipulations include biolistic transformation, a technique also well known in the art, the use of *Agrobacterium rhizogenes*, particle gun, electroporation polyethylene glycol or silica fibers.

The present invention may be applied to any plank, in particular, maize, wheat, tomato, oilseed rape, barley, sunflower, linseed, peas, beans, melon, pepper, squash, cucumber and egg plant (aubergine) and other broad acre plants.

Use of the term "one or more gene sequences encoding a polypeptide . . . " refers to any number of stretches of genetic material (preferably DNA) which can encode one or more peptides/polypeptides/proteins. Thus "polypeptides" A or B can actually comprise more than one amino acid sequence which may or may not be linked or associated. There is no restriction on the location in the parent plant genome of the one or more gene sequences. Where more than one gene sequence is present, encoding for more than one peptide/polypeptide/protein, the relationship between the encoded sequences in each parent plant is only relevant to the extent that the parent plant does not display the desired phenotype (to any significant level). When the one or more gene sequences encoding a polypeptide A are expressed in the same plant as the one or more gene sequences encoding polypeptide B, then the result, according to the invention is the phenotype of an active enzyme, a regulatory protein or a protein which affects the structural integrity of a cell. Proteins which affect the structural integrity of a cell include proteins that destabilise or create holes or ion channels in cellular membranes.

A particular application of the present invention is the production of male-sterile plants. Accordingly, the polypeptides A, B when expressed in the same plant may cause male-sterility by ablation of the tapetum. An alternative application, also of the first aspect of the invention is the expression of polypeptides A, B in the same plant which form an active enzyme, a regulatory protein or protein which affects the structural integrity of a cell, which, through cell ablation in a specific tissue results in a different phenotype, as described below.

In addition to causing male-sterility, potent hydrolases like Barnase can be used for other applications where cell ablation is needed, for example to remove an unneeded organ from a hybrid crop. This may contribute to reducing downstream processing costs. One example is the production of embryoless seeds, which is now described as follows: In the production of flour (from wheat) or semolinas (from maize or wheat) or corn flakes (from maize) or for other uses, it would be desirable to have seeds with no embryo. The use of embryo specific promoters in the first aspect of the invention above would enable ablation of embryos in seeds, in a cross dependent manner. That is, in the seeds produced by the plant containing one or more gene sequences encoding polypeptide A, pollinated with pollen from a plant containing one or more gene sequences encoding polypeptide B. Self pollination of plant a has to be prevented, for example by making plant a male-sterile. A possible production scheme for valuable embryoless maize grains would be the following: generate a plant containing one or more gene sequences encoding polypeptide A (plant a) and a plant containing one or more gene sequences encoding polypeptide B (plant b), designed so that combination of polypeptide, A and polypeptide B in one seed results in embryo ablation. FIG. 5 shows a production scheme for embryoless maize grains according to the invention.

The biochemical composition of plants can also be manipulated according to the first aspect of the invention, for example by fatty acid biosynthetic enzymes. Where the presence of an unusual but valuable fatty acid in the plant has a deleterious effect on the plant, it would be useful to be able to produce seeds with the unusual (fatty acid) oil through a cross between two lines having a normal (or quasi normal) oil composition (to the extent that each parent line is not deleteriously effected). Splitting the enzyme responsible for the valuable fatty acid biosynthesis in two or more inactive parts, provides a practical way of producing the seeds with the valuable oil. Where the enzyme responsible for the desired trait is heteromultimeric, separating the genes from the various monomers in the two parent plants is a simple way to implement the invention. More generally, this invention can be used to obtain hybrid seeds or hybrid plants with a particular phenotype which neither parent has. In particular, this invention can be used to create hybrid plants, resistant to a herbicide, via the crossing of two parent plants. Each of the parent plants expresses one or more non-functional parts of an active enzyme, regulatory protein or protein which effects the structural integrity of a cell, which is directly or indirectly responsible for herbicide resistance. As the one or more genes in each parent plant responsible for the trait will segregate independently, this will result in the gametes of such hybrid plants (especially pollen grains) giving rise to a lower transfer of the herbicide resistance trait to relatives or to weeds (in comparison with a classical single gene). If the hybrid seed is the harvested desirable product, expression of the desired trait would be restricted to the seed endosperm and embryo since these tissues are genetically hybrids.

The active enzyme, regulatory protein or protein which affects the structural integrity of a cell is preferably localised to a tissue specific (ie. present only in a selected tissue). This requires that one or both of the gene sequences encoding the polypeptides A, B are operatively linked to an appropriately stimulated promoter, eg. a tissue specific promoter so as to produce the desired phenotype. Where only one of the polypeptides is limited to expression in a selected tissue, the other polypeptide requires constitutive expression or at least an expression pattern which overlaps with that of the first polypeptide.

As described above, the expression may be seed or embryo specific and promoters for such tissue specificity are well known in the art. In the case of male-sterility, the promoter is preferably tapetum specific. Such promoters known in the art include the TA29 promoter (EP-A-0344029), the A9 promoter (Paul et al 1992, Plant Molecular Biology, vol. 19, p. 611–622) and the promoters described in WO95/29247. In order for heterozygous plants to have the desired phenotype, promoters must be active at the sporophytic level.

The choice of gene sequence for producing an active enzyme, regulatory protein or protein which affects the structural integrity of a cell depends, of course, on the desired phenotype. Any gene sequence encoding an active enzyme, regulatory protein or protein which affects the structural integrity of a cell can be used provided that the protein activity can result from the association, interaction or combination of two or more polypeptides encoded by two or more gene sequences and that their activity can result in the desired phenotype. Immediately obvious proteins which can be suitable are those which are naturally encoded by two or more polypeptides and which self-assemble to form the final protein structure. The individual polypeptide units (subunits) should have no significant activity in vivo.

Suitable proteins for use according to the invention include natural heterodimeric proteins such as the C1-R maize proteins and the Apetala3-Pistillata (Ap3-Pi) *Arabidopsis thaliana* proteins. When present in the tapetum, the dimer protein Ap3-Pi can activate genes responsive to this transcription factor (which would normally be inactive because this transcription factor is normally absent from, or present at a low level in, the tapetum). The activated gene is preferably, but not necessarily, endogenous to the plant of interest. For example, expressing the dimer Ap3-Pi in the tapetum of maize will activate transcription of genes normally involved in flower development in other floral organs, and will prevent normal pollen maturation. The level of sterility of such a system can be improved by also engineering into the daughter plant a gene sequence which is affected by the produced active enzyme or regulatory protein.

One example is the introduction into one of the parent lines of a gene sequence from Barnase or PR-Glucanase under the control of the Apetala3 promoter (pApetala3). The Apetala3 promoter is responsive to the Ap3-Pi dimer and thus expression of the Barnase or PR-Glucanase protein occurs in the daughter plant. Such a system provides for the enhancement of plant male-sterility with the additional advantage of being under a strict control mechanism (via the pApetala3). Thus, the cause of the desired phenotype may be direct, ie. a direct result of the active enzyme, regulation protein or protein which affects the structural integrity of a cell, or may be indirect, ie. acting via an intermediate factor. Other transcription factors, for use in the invention, exist already as, or can be engineered to, a heterodimeric form, for example using the dimerisation domains described below. These include artificial transcription factors made by the association of a DNA binding domain and an activation domain of different origins.

An alternative use of the Apetala3-Pistillata system, is the complementation of mutations in sub-units of the proteins. For example, one parent plant may express both proteins but with a mutation in one or the other so that the plant does not have the active dimer. The other parent plant may also express both proteins, in this case, a mutation being in the other protein. The second parent plant would not express the active dimer. A cross between the two parent plants would result in expression of genes to produce an active dimer.

Ectopic expression of the subunits for these transcription factors can be used to modulate expression of their target gene and cause male sterility or other traits (including pleiotropic effects) in a cross-dependent manner.

It is also possible to use, according to the first aspect of the invention proteins which have to be "artificially" split into two or more nucleic acid coding sequences. The resulting polypeptides/proteins must associate, assemble, interact or come together when expressed in the same plant to form an active enzyme, regulatory protein or protein which affects the structural integrity of a cell. Such artificial splitting of enzymes and proteins is today easily achieved by predicting where the protein can be split into two or more domains, for example predicting by structural biochemistry such as X-ray crystallography, functional protein analysis in mutants, structure prediction from sequence analysis or by limited proteolysis, amongst other techniques. In this way, the random coil or other suitable regions are identified as places where the protein may be split.

Examples of artificially split proteins include:

Barnase: This protein has been widely used to cause cell ablation, when expressed in specific tissues. Under the control of a tapetum specific promoter, expression of a Barnase gene causes male-sterility in many plant species (EP-A-0344029). It is known that the Barnase protein can be split into two polypeptides, which per se have no catalytic activity [in vitro]. When put together the two polypeptides can self-assemble to produce an enzyme whose product has RNase activity. (Sancho and Fersht, 1992, J.Mol.Biol., 224, 741–747).

RNase A can also be used. It was shown, as long ago as 1959 (Richards and Vithayathil, J.Biol.Chem., 234, 1459–1465) that RNase A can similarly be split by mild proteolytic treatment into two polypeptides which can then reassociate and produce an active enzyme.

In order to implement a system, according to the present invention, involving artificially split proteins, it may be necessary to design genetic constructs in order to express the polypeptides therefrom. In order to design the genetic constructs whose products will associate to form the active enzyme some modifications may be required. For example, a methionine codon can be added in front of the ORF encoding the second half of the active enzyme and a stop codon can be added after the ORF encoding the first half of the active enzyme. If the polypectides are expressed as the C terminal part of a translational fusion to another protein or to a protein targeting sequence, then a start codon may be absent from the ORF of polypeptide A and/or polypetide B, whereas a stop codon is still needed to terminate the ORF of polypeptide A and polypeptide B, respectively. If polypeptide A or B is expressed as the N-terminal part of a translational fusion to another protein, then the ORF of polypeptide A or B will start with a methionine codon whereas the termination codon is provided by the ORF of the other protein to which it is fused. Such genetic construct design is commonplace and well known to the person skilled in the art.

The invention may also be practised by expressing two portions of two different enzymes that together give a different activity than either of the intact parent proteins.

Preferably, both parent plants are homozygous with respect to the gene sequences encoding polypeptide A or polypeptide B. Such genotypes ensure that all offspring will express the active enzyme, regulatory protein or protein which affects the structural integrity of the cell.

If one or more of the polypeptides (A or B) is/are small and there are doubts that any of them will be stable in a cell, it is possible to use well-known systems wherein the small polypeptide is fused in frame to a "carrier protein" which protects it from being degraded or increases its proteolytic stability, but retains its freedom to interact with the other polypeptide(s) to form the active enzyme, regulatory protein or protein which affects the structural integrity of a cell.

The carrier protein can be chosen so that the polypeptides A or B are not affected by the fusion. One suitable carrier protein is the β-Glucuronidase (GUS) protein, which tolerates addition to its $NH_2$ end, and is a good reporter gene in plants. In this case, one can use the level of GUS activity to evaluate the expression level of the fused small polypeptide. This can be useful for screening primary transformants. Another suitable carrier protein is ubiquitin (Hondred and Vierstra, 1992, Curr. Opin. Biotechnol. 3, 147–151; Vierstra, 1996, Pant Mol. Biol., 32, 275–302). When fused in frame to the carboxy-terminus of ubiquitin, proteins accumulate significantly in the plant cytoplasm. In addition artificial ubiquitin protein fusions resemble natural ubiquitin extension proteins, e.g. UBQ1 of *Arabidopsis thaliana* (Callis et al., 1990, J. Biol. Chem., 265, 12486–12493), in that they are cleaved precisely at the C-terminus of ubiquitin (after Gly 76 by specific endogenous proteases. This process releases the "attached" protein or peptide moiety from the fusion protein and thus permits polypeptide A and B to assemble into a functional enzyme or protein. Also, for the purpose of protecting small proteins from cytoplasmic proteolysis translational products may be enlarged by fusing them to protein targeting signals, e.g. the C-terminus (Whelan and Glaser, 1997, Plant Mol. Biol. 33, 771–781) and be directed to specific locations in the cell such as to mitochondria. A suitable signal, for example, is the one found in the AOX3 protein of soybean (Finnegan and Day, Plant Physiol., 1997, 114, pp 155) which would add 50 amino acids to polypeptide A and B, respectively. Import associated proteclytic processing will remove the targeting signal by cleavage after Met50 thereby releasing the free polypeptides A and B into the mitochondria where they combine to disrupt mitochondrial function and thus to compromise cell viability.

In some cases, when expressed in two or more portions, the polypeptides may not spontaneously associate, assemble, interact or come together in vivo to reform an active protein, or regulatory enzyme or protein which affects the structural integrity of a cell. In other cases the association of the polypeptides may be weak so that little active reconstituted protein is formed. To circumvent these problems, each protein portion may be linked to a protein dimerisation domain, thus enabling the portions to be brought together in vivo. Such protein dimerisation domains are found in many proteins that naturally form dimers or multimers and the linking technique is well known in the art.

For example, the human cysteine-rich protein LIM double zinc finger motif has been fused to the Gal4 and VP16 proteins. In contrast to the unmodified Gal4 and Vp16 proteins the LIM-Gal4 and LIM-VP16 associate in vitro and in vivo (in NIH 3T3 mammalian cells) forming an active transcription factor (Feuerstein et al., 1994, Proc.Natl.Acad.Sci. U.S.A. 91, 10655–10659). The LIM motif is found in many organisms. For example, a sunflower pollen specific protein with a LIM domain has been identified (Batlz et al., 1996, Plant Physiology (Supplement III, 59). Other protein dimerisation domains exist such as the leucine zipper (Turner, R. and Tijian R., 1989 Science, 243, 1689–1694), the helix-loop-helix (Murre et al., 1989, Cell, 56, 777–783), the ankyrin Blank et al., 1993, Trends in Biochemical Sciences, 17, 135–140) and the PAS (Huang et al., 1993, Nature, 364, 259–262) domains.

One may also wish to ensure that the genes encoding polypeptides A or B are inserted in the genomes of parents a and b at an identical position (or at tightly linked positions) so that their chance of co-segregation in the transgenic hybrid is low. This can be advantageous, for example in the production of hybrid seed since the two genes that are used to create the male-sterile parent plant will subsequently segregate. Thus, F1 hybrid progeny are 100% male fertile since no hybrid plant can inherit both components of the male-sterility system.

The gene sequences carried by the parent plants a and b which encode part of the active enzyme, regulatory protein or protein which affects the structural integrity of a cell may be from a different organism. The gene sequences do not have to be plant derived and include genes from microbial or other sources. For example, the gene sequences may be Arabidopsis endogenous sequences in maize or tomato parent plants. Also, the gene sequences may be those which, in combination with a tissue specific promoter, are expressed in a tissue in which the gene sequences are not normally expressed.

According to a second aspect of the invention there is provided a method for producing a plant having a desired phenotype of an active enzyme, a regulatory protein or a protein which affects the structural integrity of a cell, the method comprising crossing a first plant line with a second plant line wherein the first line contains one or more gene sequences encoding a polypeptide A which is part of an active enzyme, regulatory protein or protein which affects the structural integrity of a cell but which line does not have the phenotype and wherein the second line contains one or more gene sequences encoding a polypeptide B which is complementary to the polypeptide or protein A but which line does not have the desired phenotype. Here, the term "complementary" means that when expressed in the same plant the polypeptides A and B associate, interact or come together to form the phenotype of an active enzyme, a regulatory protein or protein which affects the structural integrity of a cell.

Such a method may incorporate one or more of the features described above for the first aspect of the invention and the invention contemplates the application of these aspects according to the second aspect of the invention.

According to a third aspect of the invention there is provided a seed or plant obtainable from a pair of plants according to the first aspect of the invention or by a method according to the second aspect of the invention.

According to a fourth aspect of the invention there is provided a seed or plant having a phenotype of an active enzyme, regulatory protein or protein which affects the structural integrity of the cell, which is caused by the combined action of two or more transgenes, the transgenes not being present on the same copy of a chromosome. The preferred embodiments of the first, second and third aspects of the invention also apply to the fourth aspect. This means that the two or more transgenes are either on different chromosomes, or on different copies of the same chromosome, ie. the plant is made by a cross.

The invention will now be described by the following non-limiting Examples:

EXAMPLE 1

Splitting the Barnase Gene Into Two Components (FIG. 1)

The results of Sancho and Ferscht, 1992, J.Mol.Biol., 224, 741–747 show that Barnase activity can be obtained by combining a peptide A containing amino acids 1 to 36 of the mature Barnase protein and peptide B containing amino acids 37 to 110 of the mature Barnase protein. The allele of Barnase which is described in Sancho and Ferscht is a mutant which has a methionine at position 36, allowing cyanogen bromide to cleave between 36 and 37 and produce the 2 peptides. The following genetic constructs, to express the peptides, were prepared:

Peptide A:
  i. A Barnase gene with a methionine codon (amino acid position −1) added before codon 1 of the mature Barnase sequence so that translation can take place as described in Paul et al, 1992, Plant Mol.Biol., 19, 611–622.
  ii. An ORF coding for a peptide called A*, containing a methionine followed by amino acids 1 to 35 of mature Barnase protein followed by an Ochre stop codon.
  iii. A gene made of ORF A* under control of the A9 promoter by using IPCR on our plasmid p3079, which contains the AMS gene pA9-Barnase (as in i. above)—Barstar—CaMV 3' region. (See FIG. 2).

Plasmid p3079 was constructed by cloning a fragment containing the ORFs for Barnase-Barstar, obtained by PCR from pWP127 (Paul et al, 1992, supra), in our plasmid p1415, which is a derivative of pWP91 (WO-A-9211379) where the EcoRV restriction site has been converted to HindIII. IPCR was then performed on p3079 using primers B3 and B4 (see FIGS. 1 and 2) designed so that the sequence between codon 36 of Barnase and stop codon of Barstar is not part of the amplified product. The IPCR amplified sequence was then circularised by ligation and the resulting plasmid was introduced into *E. coli* The plasmid was then prepared, cut with EcORI and the fragment containing the ORF A* was cloned in the EcoRI sites of p1415, so that ORF A* would be under the control of the A9 promoter from a sequence not treated by PCR. The resulting plasmid p2022 contains ORF A* in the A9 expression cassette.

iv. An ORF coding for a peptide called A**, comprised of a start methionine codon followed by amino acids 1 to 36 of the mutant Barnase (Sancho and Ferscht, 1992, supra) but lacking a stop codon.

This was obtained by PCR on template p2022 with primers B5 (retaining the XbaI site at the 5' end) and B6 generating a blunt 3' end.

v. A gene made of the translational fusion of ORF A** and the ORF of (Gly4 Serβ/GUS under the control of the A9 promoter, the product of which shows peptide A fused in frame to the N-terminus of (Gly4 Ser)3/GUS (FIG. 1D).

This was obtained by replacing the S-peptide ORF in plasmid p2028 (see example 3) with the ORF of plasmid A (iv). For ORF replacement an IPCR was performed on plasmid p2028 using primers B7 (retaining the Xba site at the 5' end) and B8 (generating a blunt 3' end) to delete the region encoding the S-peptide from the S-peptide-GUS translational fusion. After digest with XbaI, the PCR fragment encoding peptide A (iv) was inserted XbaI/blunt into the acceptor DNA generated by IPCR.

vi. An ORF coding for peptide A*, essentially identical to peptide A(iv) but lacking a methionine start codon and containing an amber stop codon.

This was obtained by PCR on template p2022 using primers B9 (producing a blunt 5' end) and B10 (introducing a BamHI site at the 3' end). The 3' end of the PCR product was digested with BamHI for construction of the ubiquitin-petide A*** translational fusion (below).

vii. A gene made of the translational fusion of genomic DNA encoding ubiquitin and the ORF A* under the control of the A9 promoter, the product of which shows peptide A* fused in frame to the C terminus of ubiquitin (FIG. 1E).

The genomic DNA encoding ubiquitin was obtained by PCR from chromosomal DNA of *Arabidopsis thaliana*. The PCR primers Ubq16F and Ubq1R were designed to amplify the ubiquitin encoding sequence from the extension protein gene UBQ1, first described by Callis et al. (1990, supra). Restriction sites for XbaI (at 5' end) and BamHI (at 3' end), introduced during thermocycling, were used to clone the PCR fragment under the control of the A9 promoter of p1415 digested with XbaI and BamHI to yield plasmid p3245. IPCR was then performed on p3245 using primers UBQ1a and UBQ1b to generate a blunt acceptor end immediately after the ubiquitin codon Gly 76 and at the 3' end to reconstitute the BamHI restriction site for cloning. After BamHI digest this construct served as acceptor for the PCR fragment encoding peptide A*** (vi).

Peptide B:

i. An ORF coding for a peptide called B* which starts with a methionine codon followed by codons 37 to 110 of the mature Barnase sequence. In effect this transfers the methionine 36 of the mutant Barnase gene (Sancho and Ferscht, 1992, supra) from peptide A to peptide B, yielding peptides A* and B*.

ii. Gene for ORF B* containing the ATG (amino acid position −1) of Barnase (in p3079) fused to codon 37 of Barnase, under control of the A9 promoter, by deleting (by IPCR with suitable primers) (see below)) codons 1 to 36 of the mature Barnase sequence.

This was done by performing on p3079 an IPCR reaction using primers B1 and B2, (FIGS. 1 and 2) designed so that the sequence between codon 2 and codon 36 of Barnase is not part of the amplified product (see FIG. 2). The IPCR product is treated as described above for ORF A*, and cloned under control of the A9 promoter in p1415. The resulting plasmid p2023 contains ORF B*—Barstar in the A9 expression cassette.

iii. An ORF encoding peptide B*** which differs from B* (i) in that it lacks the start methionine.

iv. A gene made of the translational fusion of genomic DNA encoding ubiquitin and the ORF B* under the control of the A9 promoter, the product of which shows peptide B* fused in frame to the C-terminus of ubiquitin (FIG. 1F).

IPCR as performed on plasmid p2023 (above) with primers B11 and B12, retaining the XbaI site at the 5' end of B* but removing the ATG start and leaving a blunt 3' end. After digest with XbaI, the IPCR product served as an acceptor for the ubiquitin encoding DNA. The latter sequence was obtained by PCR from plasmid p3245 (above) with primers Ubq16F and Ubq1b retaining an XbaI site at the 5' end while leaving the 3' end blunt. After digest with XbaI, the IPCR and the PCR product were ligated to yield the translational fusion shown.

In FIG. 1G: The nucleotide sequences of primers are listed which were used for PCR and IPCR, respectively.

In FIG. 2: Circular plasmid p3079, containing the A9-driven barnase/barstar gene (FIG. 1) in p1415, served as template for Inverse PCR. As the PCR primers (FIG. 1) pointed into opposite directions, the IPCR yielded a linear double-stranded plasmid DNA from which the region in between the 5' ends of the annealed PCR primers was deleted (below). Intramolecular ligation would then yield circular deletion plasmids which were introduced into *E.coli* for further subcloning.

Also In FIG. 2-:

lane 1:

A schematic (not to scale) representation is shown of plasmid p3079. The different structural parts of the coding regions are highlighted. ATG and TAA represent the start and stop codon of barnase and barstar, respectively. The relative positions of codons 35, 36 and 37 of the mature Barnase protein are indicated.

lane 2:

IPCR with primers B1 and B2 deleted codons 1 to 36 of the mature Barnase protein. Intramolecular ligation of the linear deletion plasmid then fused the ATG start codon to codon 37 yielding the pepB*/barstar region.

lane 3:

IPCR with primers B3 and B4 deleted the sequence downstream of the barnase codon 35 as indicated. Intramolecular ligation of the linear deletion plasmid then fused the barnase codon 35 to the barstar stop codon yielding the pepA* sequence.

EXAMPLE 2

Plant Transformation With the Genetic Constructs in Example 1

Genes pA9-A* and pA9-B* expressing a polypeptide A and a polypeptide B from the A9 promoter (WO92/11379) were cloned into derivatives of the plant transformation vector pBin19 Beven et al., 1984, Nucl. Ac. Res. 12, 8711 Frish et al., 1995 Plant Mol. Biol., 27, 405–409 and Arabidopsis plants containing pA9-polypeptide A, or pA9-polypeptide B, or both genes, were obtained. Plants containing both genes were male sterile, whereas plants containing one gene were unaffected by the transgene. Plants with one gene were allowed to self, their progeny was harvested, and was analysed to identify homozygous and heterozygous T1 plants. T1 plants with pA9-polypeptide A were crossed with T1 plants with pA9-polypeptide B. The hybrid seeds obtained displayed the predicted phenotype: wild type if containing one gene only, and male sterile when containing the two genes.

Genes are introduced into maize and into tomato by biolistic or Agrobacterium-mediated transformation, and plants are regenerated and assessed for male fertility in a similar way. (Mornish et al., 1990 Biol/Technology 8, 833–839 and Fillati et al., 1987 Bio/Technology 5, 726–7390.

EXAMPLE 3

Splitting an RNAseA Gene Into two Components FIGS. 3 and 4)

From the work of Richards and Vithayathil (1959 supra), we know that the enzyme RNAseA can be cleaved (by the protease subtilisin) to generate two polypeptides: the S-peptide contains amino acids 1 to 20 of RNaseA, and the S-protein contains amino acids 21 to 124 of RNaseA. When combined, the S-peptide and the S-protein associate, and reconstitute an active enzyme. The last 5 amino acids of the S-peptide are not needed for reconstituting RNaseA: a smaller S-peptide made of amino acids 1 to 15 is sufficient. Genes which express the S-peptide and the S-protein under control of the A9 promoter were used to develop a system according to the invention.

The starting material was a synthetic gene coding for bovine pancreatic RNAseA (Vasantha and Filpula, 1989, Gene 76 53–60). A gene coding for the ORF of RNaseA was made using synthetic oligonucleotides (see FIGS. 3A and 3B). The nucleotide sequence of the gene was designed to be compatible with maize codon usage, according to Fennoy and Bailey-Serres, 1993 Nuc. Acids Res., 21, 5294–5300. PCR with suitable primers was used to amplify from the full length ORF. The following ORPS were built:

S-peptide:

i. An ORF for the S-peptide containing a methionine translation initiation codon followed by codons 1 to 15 of the mature RNAseA sequence (see FIGS. 4A and 4B) and terminated by an Ochre stop codon.

ii. An ORF made of a methionine translation initiation codon followed by codons 1 to 15 of the mature RNAseA sequence, followed by a linker sequence encoding (Gly4-Ser)3 (see FIGS. 4A and 4B). This gene was designed so that it can be fused in frame to the ORF of the GUS protein by cloning in the BamHI site of plasmid p2027 which contains the GUS-gene from pBI101.3 (Jefferson, 1987 Plant Mol.Biol.Reporter, 5 387–405).

iii. A translational fusion comprising the ORF of the mitochondrial protein targeting sequence of AOX3 protein from soybean (Finnegan and Day, 1997, Plant Physiol. 114, pp455) and the ORF of S-peptide as described in (i) but lacking the methionine translation initiation codon (FIG. 4C). The gene product of said translational fusion shows the S-peptide fused to the C-terminal end of the targeting sequence.

iv. A translational fusion comprising the ORF of the mitochondrial protein targeting sequence of AOX3 protein (supra) and the ORF of the S-peptide-GUS fusion as described in (ii) but lacking the methionine translational initiation codon (FIG. 4C). The gene product of said translational fusion shows that the S-peptide-GUS protein fused to the C-terminal end of the targeting sequence.

S-protein:

i. An ORF for the "S-protein +5", which contains a methionine translation initiation codon followed by codons 16 to 124 of mature RNAseA sequence and is terminated by an Ochre codon.

ii. An ORF for the S-protein which contains a methionine translation initiation codon followed by codons 21 to 124 of mature RNAgeA sequence and is terminated by an Ochre codon.

iii. A translational fusion comprising the ORF of the mitochondrial protein targeting sequence of AOX3 protein (supra) and the ORF of the S-protein as described in (ii) but lacking the methionine translational intitiation codon (FIG. 4C). The gene product of said translational fusion shows the S-protein fused to the C-terminal end of ubiquitin.

iv. A translational fusion comprising genomic DNA encoding ubiquitin and the ORF of the S-protein as described in (ii) but lacking the methionine translational intitiation codon (FIG. 4C). The gene product of said translational fusion shows the S-protein fused to the C-terminus of ubiquitin.

Genes under control of the A9 promoter were then built and introduced into plants as in Example 2.

In FIG. 3A: The sequences encoding the S-peptide, the S(+5)-protein and the S-protein were constructed by first aligning sense oligonucleotides RN-I to RN-VII lanes 2, 5, 7, 9, 11, 13, 16) along complementary guide oligonucleotides RN-1 to RN-6 (lanes 3, 6, 8, 10, 12, 14) and then selectively ligating the correctly aligned sense oligonucleotides using Taq-DNA-Ligase.

The ligation resulted in a continuous single DNA strand sense) which was subsequently amplified by Vent DNA polymerase (25 PCR cycles) using one of two primer pairs as follows: (i) Primers RN-a (lane 1) and RN-b (lane 15) amplified the full ligation product. The PCR product was gel purified and cleaved with restriction enzymes BamHI (underlined, lanes 1 and 15) and BglII underlined, lanes 2 and 4) to yield two DNA fragments encoding the S-peptide and the S(+5) protein. The two fragments were cloned separately into the BamHI site downstream of the pA9 promoter in plasmid p14l5 to yield plasmids p4837 (S-peptide) and p4838 (S+5 protein). (ii) Primers RN-d (lane 4) and RN-b (lane, 15) amplified the coding sequence of the S-protein. The PCR product was cloned as described in (i) to yield plasmid p4839 (S-protein).

lane 1: PCR primer (sense) RN-a lane 2: Oligonucleotide RN-I and alignment to oligonucleotide RN-II lane 3: Guide oligonucleotide RN-1 (antisense)

lane 4: PCR primer (sense) RN-d lane 5: oligonucleotide RN-II (continued from lane 2) and alignment to oligonucleotide RN-IIIN lane 6: Guide oligonucleotide RN-2N (antisense)

lane 7: oligonucleotide RN-IIIN (continued from lane 5) and alignment to oligonucleotide RN-IV lane 8: Guide oligonucleotide RN-3 (antisense)

lane 9: oligonucleotide RN-IV (continued from lane 7) and alignment to oligonucleotide RN-V lane 10: Guide oligonucleotide RN-4 (antisense)

lane 11: oligonucleotide RN-V (continued from lane 9) and alignment to oligonucleotide RN-VI lane 12: Guide oligonucleotide RN-5 (antisense)

lane 13: oligonucleotide RN-VI (continued from lane 11 and alignment to oligonucleotide RN-VII lane 14: Guide oligonucleotide RN-6 (antisense)

lane 15: PCR primer (antisense) RN-b
lane 16: oligonucleotide RN-VII (continued from lane 13)
Symbols:
(5'): non-phosphorylated 5' end
(5P): phosphorylated 5' end
(3OH): conventional 3' end
(small letters): bases added for the convenience of cloning.

In FIG. 3B: The sequences encoding the S-peptide with the (Gly$_4$Ser)$_3$-linker peptide were constructed by first aligning sense oligonucleotides RN-I and RN-VIII (lanes 2 and 4) along the complementory guide oligonucleotide RN-7, and then selectively ligating the correctly aligned oligonucleotides using Taq-DNA-Ligase.

The ligation resulted in a continuous single DNA strand which was subsequently amplified by Vent DNA polymerase (25 PCR cycles) using the primer pair RN-a (lane 1) and RN-c (lane 5). This PCR reaction yielded the full length, double stranded ligation product. The PCR product was gel purified, then cleaved with restriction enzymes BamHI (underlined, lane 1) and BglII (underlined, lane 5) and cloned into the BamHI site of p2027 to generate an NH$_2$-terminal protein fusion to GUS under the control of the pA9 promoter (p2027 was constructed by cloning the GUS coding sequence of pBI101.3 as a BamHI/SmaI fragment into the BamHI site of p1415). This yielded plasmid p2028.

lane 1: PCR primer (sense) RN-a
lane 2: Oligonucleotide RN-I encoding the S-peptide as in FIG. 3a and the alignment to oligonucleotide RN-VIII encoding the (Gly4-Ser)3 linker peptide
lane 3: Guide oligonucleotide (antisense) RN-7
lane 4: Oligonucleotide RN-VIII (continued from lane 2)
lane 5: PCR primer (antisense) RN-c
Symbols:
(5'): non-phosphorylated 5' end
(5P): phosphorylated 5' end
(3OH): conventional 3' end
(small letters): bases added for the convenience of cloning In FIG. 4A: The protein and DNA sequence is shown for S-peptide and the S-peptide with (Gly4 Ser)3 linker. The S-peptide linker sequence was fused in frame to GUS to yield plasmid p2028 as described for FIG. 3B.

In FIG. 4B: The ORF for (S+5)-protein and S-protein is shown as contained in plasmids p4838 and p4839, respectively. These plasmids were described above for FIG. 3A.

In FIG. 4C:
(i) The mitochondrial protein targeting sequence (short of the last four amino acids: Leu-Arg-Arg-Met) was obtained by PCR with primers AOX3MI1 and AOX3MI2 from a plasmid which contained the cDNA of Alternative Oxidase (AOX3) of soybean as published by Finnegan and Day, 1997 (Plant Physiol. 114; pp455). Restriction sites (XbaI and BglII at the 5' end and AflII and BamHI at the 3' end) were introduced during the thermocycling to yield the PCR product which was cloned XbaI/BamHI downstream of the A9 promoter in p1415. This plasmid was called p0200.
(ii) Primers SPEPMI1 and SPEPMI2 were then used to produce from plasmid p4837 a PCR fragment encoding within and downstream of an AflII restriction site the missing four amino acids (Leu-Arg-Arg-Met) of the mitochondrial targeting signal followed by the ORF of S-peptide. A PCR generated BamHI site at the 3' end allowed cloning of the PCR fragment as an AflII/BamHI fragment into p0200. This cloning yielded plasmid p0203, containing the complete ORF of the translational fusion as shown.
(iii) The translational fusion of mitochondial targeting sequence and ORF of S-peptide-GUS was generated in a similar fashion as described in (ii) except that PCR primers SPEPMI1 and SPEPMI2 were used on template p2028 to generate an AflII/BamHI fragment that was cloned into p0200 to yield p0204.
(iv) The translational fusion of mitochondrial targeting sequence and ORF of S-protein was generated in a similar fashion as described in (ii and iii), except that PCR primers SPROTMI1 and SPROTMI2 were used ontemplate p4838 to generate an AflII/BamHI fragment that was cloned into p0200 to yield p0202.
(v) A PCR fragment was generated from template p4839 with primers SPROTF and SPROTR containing the ORF of S-protein in between BamHI restriction sites at either end. After digestion with BamHI this PCR fragment was cloned into the BamHI site of p3245 which yielded the translational fusion in p3249 of genomic ubiquitin DNA and S-protein as shown.

EXAMPLE 4

Use of the Dimer Protein Apetala3-Pistillata

Apetala3 (Ape3) and Pistillata (Pi) are two proteins of *Arabidopsis thaliana* which are involved in the regulation of floral differentiation. The genes are known while the endogenous pattern of expression in the tapetum is not known. Expression of the Arabidopsis genes in the maize tapetum leads to disruption of the normal anther development by activating normally silent genes. These genes can also be used to activate, in the maize tapetum, an Arabidopsis promoter responsive to the Ap3-Pi dimer such as the Ap3 promoter (pAp3) itself.

We have built the following genes:
pA9 -Apetala3
The cDNA for Ap3 (Jack et al, 1992, Cell 68, 683–697 GenBank Accession No. M86357) was cloned in the A9 expression cassette of pWP91 (WO-A-9211379) giving plasmid p4796. This plasmid contains the Ap3 cDNA with approximately 15 bases of 5' untranslated sequence followed by the whole ORF (698 bases from ATG to TAA) followed by approximately 120 bases of 3' untranslated sequence, cloned in the BamHI site of pWP91.
pA9-Pistillata
The cDNA for Pi (Goto and Meyerowitz, 1994, Genes Dev. 8, 1548–1560 GenBank Accession No. D30807) was cloned in the A9 expression cassette of pWP91 (WO-A-9211379) giving plasmid p0160. This plasmid contains the Pi cDNA with approximately 24 bases of 5' untranslated sequence followed by the whole ORF (626 bases from ATG to TGA) followed by approximately 250 bases of 3' untranslated sequence, cloned in the XbaI-BamHI sites of pWP91.
pApetala3-PRGlucanase
The A9 promoter sequence in plasmid A9PR (described in Worrall et al, 1992, The Plant Cell, 4, 759–771) was replaced by a 1250 bp (approx) sequence containing the Ap3 promoter region, obtained by PCR amplification of *Arabidopsis thaliana* genomic DNA, according to the published sequence (Jack et al, 1994 Cell, 76, 703–716), giving plasmid p4817.

The genes were introduced in maize in various combinations, by biolistic transformation techniques known in the art. Plants were regenerated and assessed for male fertility.
p4796 (pA9-Ap3)/p0180 (pA9-Pi) cause male sterility. Neither of them alone causes male sterility.
p4796/p0180/p4817 (pAp3-PRGlucanase) cause sterility, when p4817 with only one of the two transcription factor genes does not.

What is claimed is:

1. A pair of parent plants for producing seeds comprising:
   (i) a first parent plant containing one or more gene sequences encoding a polypeptide A, and
   (ii) a second parent plant containing one or more gene sequences encoding a polypeptide B;
      wherein each of A and B, when expressed in a plant that expresses only one of A or B, is not an active enzyme, is not a regulatory protein and is not a protein which affects the functionality and/or viability and/or the structural integrity of a cell, but when expressed in a plant that expresses both A and B, A and B form an active enzyme, or a regulatory protein, or a protein which affects the structural integrity of a plant cell,
      wherein the one or more gene sequences encoding polypeptide A or B comprises a tapetum-specific promoter, an embryo-specific promoter, or a seed specific promoter; and
      wherein one or both of the polypeptides A or B is fused to a carrier protein or a protein targeting signal.

2. A pair of plants as claimed in claim 1, wherein the one or more gene sequences from at least one of the plants is a transgene.

3. The pair of plants as claimed in claim 1, wherein the polypeptides A and B, when expressed in the same plant, cause cell ablation.

4. The pair of parent plants as claimed in claim 1, wherein one of the parent plants is male-sterile.

5. The pair of plants as claimed in claim 1 wherein the polypeptides A and B are two polypeptide subunits of an enzyme having RNase activity.

6. The pair of plants as claimed in claim 1, wherein the polypeptides A and B are artificially split polypeptides of an active enzyme, regulatory protein or protein which affects the structural integrity of a cell.

7. The pair of plants as claimed in claim 1, wherein each patent plant is homozygous with respect to the one or more gene sequences encoding polypeptide A or B respectively.

8. The pair of plants as claimed in claim 3, wherein the cause of male-sterility is direct or indirect.

9. The pair of plants as claimed in claim 1, wherein the one or more gene sequences encoding polypeptide A or B comprises a tapetum-specific promoter.

10. The pair of plants as claimed in claim 1, wherein the one or more gene sequences from at least one of the parent plants is a heterologous gene sequence.

11. A method for producing a plant having a desired phenotype by virtue of an active enzyme, a regulatory protein or a protein which affects the structural integrity of a cell, the method comprising crossing a first plant with a second plant wherein the first plant contains one or more gene sequences encoding a polypeptide A but which plant does not have the desired phenotype and wherein the second plant contains one or more gene sequences encoding a polypeptide B but which plant does not have the desired phenotype, wherein each of A and B, when expressed in a plant that expresses only one of A or B, is not an active enzyme, is not a regulatory protein and is not a protein which affects the functionality and/or viability and/or the structural integrity of a cell, but when expressed in a plant that expresses both A and B, A and B form an active enzyme, a regulatory protein, or a protein which affects the structural integrity of a plant cell,
   wherein the one or more gene sequences encoding polypeptide A or B comprises a tapetum-specific promoter, an embryo-specific promoter, or a seed specific promoter; and
   wherein one or both of the polypeptides A and B is fused to a carrier protein or protein targeting signal.

12. The method of claim 11, wherein the one or more gene sequences from at least one of the first and the second plant is a transgene.

13. The method as claimed in claim 11, wherein the desired phenotype is cell ablation.

14. The method as claimed in claim 11, wherein one of the first plant or the second plant is male-sterile.

15. The method as claimed in claim 11 wherein the polypeptides A and B are two polypeptide subunits of an enzyme having RNase activity.

16. The method as claimed in claim 11, wherein the polypeptides A and B are artificially split polypeptides of an active enzyme, regulatory protein or protein which affects the structural integrity of a cell.

17. The method as claimed in claim 11, wherein each of the first and second plants is homozygous with respect to the gene sequence encoding polypeptide A or B, respectively.

18. The method as claimed in claim 11, wherein the desired phenotypic trait is direct or indirect male-sterility.

19. The method as claimed in claim 11, wherein the one or more gene sequences encoding polypeptide A or B comprises a tapetum-specific promoter.

20. The method as claimed in claim 11, wherein at least one of the first or second plants contains, as the one or more gene sequences, heterologous gene sequences.

21. A seed obtained by crossing the pair of plants of claim 1, or a plant obtained from the seed, wherein the seed comprises the one or more gene sequences encoding polypeptide A and the one or more gene sequences encoding polypeptide B.

22. A seed or plant, having a phenotype by virtue of an active enzyme, a regulatory protein or a protein which affects the structural integrity of a cell, which is caused by the combined action of two or more transgenes, comprising a first transgene encoding a polypeptide A and a second transgene encoding a polypeptide B wherein each of A and B, when expressed in a plant that expresses only one of A or B, is not an active enzyme, is not a regulatory protein and is not a protein which affects the functionality and/or viability and/or the structural integrity of a cell, but when expressed in a plant that expresses both A and B, A and B form an active enzyme, a regulatory protein, or a protein which affects the structural integrity of a plant cell,
   wherein the transgene encoding polypeptide A or B comprises a tapetum-specific promoter, an embryo-specific promoter, or a seed specific promoter; and
   wherein one or both of the polypeptides A and B is fused to a carrier protein or protein targeting signal.

23. A seed or progeny plant obtained from the plant of claim 21, wherein the seed or progeny plant comprises the one or more gene sequences encoding polypeptide A and the one or more gene sequences encoding polypeptide B.

24. The pair of plants as claimed in claim 3, wherein the cell ablation causes male-sterility.

25. The pair of plants as claimed in claim 3, wherein the cell ablation causes embryoless seeds.

26. The method as claimed in claim 13, wherein the cell ablation causes male sterility.

27. The method as claimed in claim 13, wherein the cell ablation causes embryoless seeds.

28. The plant as claimed in claim 21 which is male sterile.

29. A seed or progeny plant obtained from the male sterile plant of claim 28, wherein the seed or progeny plant comprises the one or more gene sequences encoding polypeptide A and the one or more gene sequences encoding polypeptide or B.

30. The seed or plant as claimed in claim 22, wherein the phenotype of the plant is male sterility.

31. A seed or progeny plant obtained from the male sterile plant of claim 30, wherein the seed or progeny plant comprises the one or more gene sequences encoding polipeptide A and the one or more gene sequences encoding polypeptide B.

32. A pair of parent plants for producing seeds comprising:
   (i) a first parent plant containing a gene sequence encoding a polypeptide A* comprising a methionine codon followed by amino acids 1 to 35 or 1 to 36 of mature Barnase; and
   (ii) a second parent plant containing a gene sequence encoding a polypeptide B* comprising a methionine codon followed by amino acids 37 to 110 of mature Barnase,
       wherein each of A* and B*, when expressed in a plant that expresses only one of A* or B*, is not an active RNese enzyme, but when expressed in a plant that expresses both A* and B*, A* and B* form an active RNase enzyme,
       wherein the one or both gene sequences encoding polypeptide A* or B* comprises a tapetum-specific promoter, an embryo-specific promoter, or a seed specific promoter; and
       wherein one or both of the polypeptides A* or B* is fused to a carrier protein or a protein targeting signal.

33. The pair of parent plants of claim 32, wherein said carrier protein or protein targeting signal is GUS.

34. A method of producing a male sterile plant by virtue of an active RNase enzyme the method comprising crossing;
   (i) a first parent plant containing a gene sequence encoding a polypeptide A* comprising a methionine codon followed by amino acids 1 to 35 or 1 to 36 of mature Barnase with
   (ii) a second parent plant containing a gene sequence encoding a polypeptide B* comprising a methionine codon followed by amino acids 37 to 110 of mature Barnase,
       wherein each of A* and B*, when expressed in a plant that expresses only one of A* or B*, is not an active RNase enzyme, but when expressed in a plant that expresses both A* and B*, A* and B* form an active RNase enzyme,
       wherein the one or both gene sequences encoding polypeptide A* or B* comprises a tapetum-specific promoter, an embryo-specific promoter, or a seed specific promoter; and
       wherein one or both of the polypeptides A* or B* is fused to a carrier protein or a protein targeting signal.

35. The method according to claim 34, wherein said carrier protein or protein targeting signal is GUS.

36. A seed or plant obtained by a process comprising crossing the pair of parent plants as claimed in claim 33, wherein said seed or plant contains said one or more gene sequence encoding polypeptide A* and the one or more gene sequences encoding polypeptide B*.

37. The seed or plant of claim 36, said seed or plant having a phenotype by virtue of an active enzyme, a regulatory protein or a protein which affects the structural integrity of a cell, which phenotype is caused by the combined action of two or more transgenes that are not present on the same copy of a chromosome.

38. The seed or plant obtained from the progeny plant produced by the method as claimed in claim 34 wherein said seed or plant contains said one or more gene sequence encoding polypeptide A* and the one or more gene sequences encoding polypeptide B*.

39. The seed obtained from the plant of claim 36 or 48.

40. The pair of plants of claim 5, wherein the enzyme having RNase activity is Barnase or RNase A.

41. The method of claim 15, wherein the enzyme having RNase activity is Barnase or RNase A.

* * * * *

SEQUENCE LISTING

<160> NUMBER OF SEQ ID NOS: 68

<210> SEQ ID NO 1
<211> LENGTH: 344
<212> TYPE: DNA
<213> ORGANISM: Plant-Unknown
<220> FEATURE:
<221> NAME/KEY: CDS
<222> LOCATION: (9)..(344)
<223> OTHER INFORMATION: :

<400> SEQUENCE: 1

```
tctagacc atg gca cag gtt atc aac acg ttt gac ggg gtt gcg gat tat      50
         Met Ala Gln Val Ile Asn Thr Phe Asp Gly Val Ala Asp Tyr
         1               5                   10 ctt cag aca tat cat aag cta cct gat aat tac att aca aaa tca gaa       98
Leu Gln Thr Tyr His Lys Leu Pro Asp Asn Tyr Ile Thr Lys Ser Glu
15              20                  25                  30 gca caa gcc ctc ggc tgg gtg gca tca aaa ggg aac ctt gca gac gtc      146
Ala Gln Ala Leu Gly Trp Val Ala Ser Lys Gly Asn Leu Ala Asp Val
                35                  40                  45 gct ccg ggg aaa agc atc ggc gga gac atc ttc tca aac agg gaa ggc      194
Ala Pro Gly Lys Ser Ile Gly Gly Asp Ile Phe Ser Asn Arg Glu Gly
            50                  55                  60 aaa ctc ccg ggc aaa agc gga cga aca tgg cgt gaa gcg gat att aac      242
Lys Leu Pro Gly Lys Ser Gly Arg Thr Trp Arg Glu Ala Asp Ile Asn
65                  70                  75 tat aca tca ggc ttc aga aat tca gac cgg att ctt tac tca agc gac      290
Tyr Thr Ser Gly Phe Arg Asn Ser Asp Arg Ile Leu Tyr Ser Ser Asp
    80                  85                  90 tgg ctg att tac aaa aca acg gac cat tat cag acc ttt aca aaa atc      338
Trp Leu Ile Tyr Lys Thr Thr Asp His Tyr Gln Thr Phe Thr Lys Ile
95                  100                 105                 110 aga taa                                                              344
Arg
```

<210> SEQ ID NO 2
<211> LENGTH: 111
<212> TYPE: PRT
<213> ORGANISM: Plant-Unknown
<220> FEATURE:
<223> OTHER INFORMATION: :

<400> SEQUENCE: 2

```
Met Ala Gln Val Ile Asn Thr Phe Asp Gly Val Ala Asp Tyr Leu Gln
1               5                   10                  15

Thr Tyr His Lys Leu Pro Asp Asn Tyr Ile Thr Lys Ser Glu Ala Gln
            20                  25                  30

Ala Leu Gly Trp Val Ala Ser Lys Gly Asn Leu Ala Asp Val Ala Pro
        35                  40                  45

Gly Lys Ser Ile Gly Gly Asp Ile Phe Ser Asn Arg Glu Gly Lys Leu
    50                  55                  60

Pro Gly Lys Ser Gly Arg Thr Trp Arg Glu Ala Asp Ile Asn Tyr Thr
65                  70                  75                  80

Ser Gly Phe Arg Asn Ser Asp Arg Ile Leu Tyr Ser Ser Asp Trp Leu
                85                  90                  95

Ile Tyr Lys Thr Thr Asp His Tyr Gln Thr Phe Thr Lys Ile Arg
            100                 105                 110
```

```
<210> SEQ ID NO 3
<211> LENGTH: 18
<212> TYPE: DNA
<213> ORGANISM: Artificial
<220> FEATURE:
<223> OTHER INFORMATION: Figure 1A: B1 primer

<400> SEQUENCE: 3
catggtctag agtacttg                                                       18

<210> SEQ ID NO 4
<211> LENGTH: 16
<212> TYPE: DNA
<213> ORGANISM: Artificial
<220> FEATURE:
<223> OTHER INFORMATION: Figure 1A: B4 Primer

<400> SEQUENCE: 4
ccagccgagg gcttgt                                                         16

<210> SEQ ID NO 5
<211> LENGTH: 16
<212> TYPE: DNA
<213> ORGANISM: Artificial
<220> FEATURE:
<223> OTHER INFORMATION: Figure 1A: B2 Primer

<400> SEQUENCE: 5
gcatcaaaag ggaacc                                                         16

<210> SEQ ID NO 6
<211> LENGTH: 228
<212> TYPE: DNA
<213> ORGANISM: Artificial
<220> FEATURE:
<223> OTHER INFORMATION: Figure 1B: Synthetic Intergenic Sequence

<400> SEQUENCE: 6
cgaaaaaaac ggcttcctgc ggaggccgtt tttttcagct ttacataaag tgtgtaataa         60
attttttctt aaactctgat cggtcaattt cactttccgg atccggtcca atctgcagcc       120
gtccgagaca ggaggacatc gtccagctga accggggca gaatccggcc atttctgaag        180
agaaaaatgg taaactgata gaataaaatc ataagaaagg agccgcac                    228

<210> SEQ ID NO 7
<211> LENGTH: 323
<212> TYPE: DNA
<213> ORGANISM: Plant-Unknown
<220> FEATURE:
<221> NAME/KEY: CDS
<222> LOCATION: (1)..(273)
<223> OTHER INFORMATION: :

<400> SEQUENCE: 7 atg aaa aaa gca gtc att aac ggg gaa caa atc aga agt atc agc gac          48
Met Lys Lys Ala Val Ile Asn Gly Glu Gln Ile Arg Ser Ile Ser Asp
1               5                   10                  15 ctc cac cag aca ttg aaa aag gag ctt gcc ctt ccg gaa tac tac ggt          96
Leu His Gln Thr Leu Lys Lys Glu Leu Ala Leu Pro Glu Tyr Tyr Gly
                20                  25                  30 gaa aac ctg gac gct tta tgg gat tgt ctg acc gga tgg gtg gag tac         144
Glu Asn Leu Asp Ala Leu Trp Asp Cys Leu Thr Gly Trp Val Glu Tyr
            35                  40                  45 ccg ctc gtt ttg gaa tgg agg cag ttt gaa caa agc aag cag ctg act         192
Pro Leu Val Leu Glu Trp Arg Gln Phe Glu Gln Ser Lys Gln Leu Thr
```

```
                   50                  55                  60
gaa aat ggc gcc gag agt gtg ctt cag gtt ttc cgt gaa gcg aaa gcg      240
Glu Asn Gly Ala Glu Ser Val Leu Gln Val Phe Arg Glu Ala Lys Ala
 65                  70                  75                  80 gaa ggc tgc gac atc acc atc ata ctt tct taa tacgatcaat gggagatgaa   293
Glu Gly Cys Asp Ile Thr Ile Ile Leu Ser
                 85                  90 caatatagat cccccgggct gcaggaattc                                     323
```

<210> SEQ ID NO 8
<211> LENGTH: 90
<212> TYPE: PRT
<213> ORGANISM: Plant-Unknown
<220> FEATURE:
<223> OTHER INFORMATION: :

<400> SEQUENCE: 8

```
Met Lys Lys Ala Val Ile Asn Gly Glu Gln Ile Arg Ser Ile Ser Asp
 1               5                  10                  15

Leu His Gln Thr Leu Lys Lys Glu Leu Ala Leu Pro Glu Tyr Tyr Gly
                20                  25                  30

Glu Asn Leu Asp Ala Leu Trp Asp Cys Leu Thr Gly Trp Val Glu Tyr
            35                  40                  45

Pro Leu Val Leu Glu Trp Arg Gln Phe Glu Gln Ser Lys Gln Leu Thr
    50                  55                  60

Glu Asn Gly Ala Glu Ser Val Leu Gln Val Phe Arg Glu Ala Lys Ala
 65                  70                  75                  80

Glu Gly Cys Asp Ile Thr Ile Ile Leu Ser
                85                  90
```

<210> SEQ ID NO 9
<211> LENGTH: 21
<212> TYPE: DNA
<213> ORGANISM: Artificial
<220> FEATURE:
<223> OTHER INFORMATION: Figure 1C: B3 Primer

<400> SEQUENCE: 9

```
taatacgatc aatgggagat g                                               21
```

<210> SEQ ID NO 10
<211> LENGTH: 194
<212> TYPE: DNA
<213> ORGANISM: Artificial
<220> FEATURE:
<223> OTHER INFORMATION: Figure 1D
<220> FEATURE:
<221> NAME/KEY: CDS
<222> LOCATION: (9)..(194)

<400> SEQUENCE: 10

```
tctagacc atg gca cag gtt atc aac acg ttt gac ggg gtt gcg gat tat    50
         Met Ala Gln Val Ile Asn Thr Phe Asp Gly Val Ala Asp Tyr
          1               5                  10 ctt cag aca tat cat aag cta cct gat aat tac att aca aaa tca gaa    98
Leu Gln Thr Tyr His Lys Leu Pro Asp Asn Tyr Ile Thr Lys Ser Glu
 15                  20                  25                  30 gca caa gcc ctc ggc tgg atg ggc ggt ggc ggt tcc ggt ggc ggt ggc   146
Ala Gln Ala Leu Gly Trp Met Gly Gly Gly Gly Ser Gly Gly Gly Gly
                35                  40                  45 agc ggc ggc ggt ggt agc ggg atc ccc ggg tac ggt cag tcc ctt atg   194
Ser Gly Gly Gly Gly Ser Gly Ile Pro Gly Tyr Gly Gln Ser Leu Met
```

<210> SEQ ID NO 11
<211> LENGTH: 62
<212> TYPE: PRT
<213> ORGANISM: Artificial
<220> FEATURE:
<223> OTHER INFORMATION: Figure 1D

<400> SEQUENCE: 11

Met Ala Gln Val Ile Asn Thr Phe Asp Gly Val Ala Asp Tyr Leu Gln
1               5                   10                  15
Thr Tyr His Lys Leu Pro Asp Asn Tyr Ile Thr Lys Ser Glu Ala Gln
            20                  25                  30
Ala Leu Gly Trp Met Gly Gly Gly Ser Gly Gly Gly Ser Gly
        35                  40                  45
Gly Gly Gly Ser Gly Ile Pro Gly Tyr Gly Gln Ser Leu Met
    50                  55                  60

<210> SEQ ID NO 12
<211> LENGTH: 526
<212> TYPE: DNA
<213> ORGANISM: Artificial
<220> FEATURE:
<223> OTHER INFORMATION: Figure 1E

<400> SEQUENCE: 12
tctagaccat gcagatcttc gtgaaaacct tgaccggcaa gaccatcact ctcgaggtcg    60
agagcagcga caccatcgac aatgtcaagg ccaagatcca agacaaagaa ggtatcattc   120
ttcctcactc aatctggatt cttctcttta gcttttgaa attcagatct cttatcattt    180
acttgtttct cctttaagga atccctccgg atcagcagag attgatcttc gccggaaagc   240
agctcgaaga tggccgtact ttggctgact acaacatcca gaaaggtacg aaatcatccg   300
aatccttctg ttgatcattt cgatgatctg attgtataaa ctctaatgga ttgttatcat   360
ttgtaaacag aatctacact tcatcttgtg ttgaggctta gaggtggagc acaggttatc   420
aacacgtttg acggggttgc ggattatctt cagacatatc ataagctacc tgataattac   480
attacaaaat cagaagcaca agccctcggc tggatgtaga ggatcc                  526

<210> SEQ ID NO 13
<211> LENGTH: 631
<212> TYPE: DNA
<213> ORGANISM: Artificial
<220> FEATURE:
<223> OTHER INFORMATION: Figure 1F

<400> SEQUENCE: 13
tctagaccat gcagatcttc gtgaaaacct tgaccggcaa gaccatcact ctcgaggtcg    60
agagcagcga ccatcgacaa tgtcaaggcc aagatccaag acaaagaagg tatcattctt   120
cctcactcaa tctggattct tctctttagc tttttgaaat tcagatctct tatcatttac   180
ttgtttctcc tttaaggaat ccctccggat cagcagagat tgatcttcgc cggaaagcag   240
ctcgaagatg gccgtacttt ggctgactac aacatccaga aggtacgaa atcatccgaa    300
tccttctgtt gatcatttcg atgatctgat tgtataaact ctaatggatt gttatcattt    360
gtaaacagaa tctacacttc atcttgtgtt gaggcttaga ggtggagcat caaaagggaa   420
ccttgcagac gtcgctccgg ggaaaagcat cggcggagac atcttctcaa acagggaagg   480
caaactcccg ggcaaaagcg gacgaacatg gcgtgaagcg gatattaact atacatcagg   540

```
cttcagaaat tcagaccgga ttctttactc aagcgactgg ctgatttaca aaacaacgga      600
ccattatcag acctttacaa aaatcagata a                                     631
```

<210> SEQ ID NO 14
<211> LENGTH: 20
<212> TYPE: DNA
<213> ORGANISM: Artificial
<220> FEATURE:
<223> OTHER INFORMATION: Figure 1G: B5

<400> SEQUENCE: 14

```
cacaagtact ctagaccatg                                                   20
```

<210> SEQ ID NO 15
<211> LENGTH: 19
<212> TYPE: DNA
<213> ORGANISM: Artificial
<220> FEATURE:
<223> OTHER INFORMATION: Figure 1G: B6

<400> SEQUENCE: 15

```
catccagccg agggcttgt                                                    19
```

<210> SEQ ID NO 16
<211> LENGTH: 16
<212> TYPE: DNA
<213> ORGANISM: Artificial
<220> FEATURE:
<223> OTHER INFORMATION: Figure 1G: B7

<400> SEQUENCE: 16

```
ggcggtggcg gttccg                                                       16
```

<210> SEQ ID NO 17
<211> LENGTH: 23
<212> TYPE: DNA
<213> ORGANISM: Artificial
<220> FEATURE:
<223> OTHER INFORMATION: Figure 1G: B8

<400> SEQUENCE: 17

```
ccactagttc tagagtactt gtg                                               23
```

<210> SEQ ID NO 18
<211> LENGTH: 18
<212> TYPE: DNA
<213> ORGANISM: Artificial
<220> FEATURE:
<223> OTHER INFORMATION: Figure 1G: B9

<400> SEQUENCE: 18

```
gcacaggtta tcaacacg                                                     18
```

<210> SEQ ID NO 19
<211> LENGTH: 31
<212> TYPE: DNA
<213> ORGANISM: Artificial
<220> FEATURE:
<223> OTHER INFORMATION: Figure 1G: B10

<400> SEQUENCE: 19

```
gcggatcctc tacatccagc cgagggcttg t                                      31
```

<210> SEQ ID NO 20

```
<211> LENGTH: 16
<212> TYPE: DNA
<213> ORGANISM: Artificial
<220> FEATURE:
<223> OTHER INFORMATION: Figure 1G: B11

<400> SEQUENCE: 20
gcatcaaaag ggaacc                                                        16

<210> SEQ ID NO 21
<211> LENGTH: 17
<212> TYPE: DNA
<213> ORGANISM: Artificial
<220> FEATURE:
<223> OTHER INFORMATION: Figure 1G: B12

<400> SEQUENCE: 21
ggtctagagt acttgtg                                                       17

<210> SEQ ID NO 22
<211> LENGTH: 30
<212> TYPE: DNA
<213> ORGANISM: Artificial
<220> FEATURE:
<223> OTHER INFORMATION: Figure 1G: Ubq16F

<400> SEQUENCE: 22
gctctagacc atgcagatct tcgtgaaaac                                         30

<210> SEQ ID NO 23
<211> LENGTH: 25
<212> TYPE: DNA
<213> ORGANISM: Artificial
<220> FEATURE:
<223> OTHER INFORMATION: Figure 1G: Ubq1R

<400> SEQUENCE: 23
ctggatccac ctctaagcct caaca                                              25

<210> SEQ ID NO 24
<211> LENGTH: 24
<212> TYPE: DNA
<213> ORGANISM: Artificial
<220> FEATURE:
<223> OTHER INFORMATION: Figure 1G: Ubq1a

<400> SEQUENCE: 24
tatggatccc ccgggctgca ggaa                                               24

<210> SEQ ID NO 25
<211> LENGTH: 21
<212> TYPE: DNA
<213> ORGANISM: Artificial
<220> FEATURE:
<223> OTHER INFORMATION: Figure 1G: Ubq1b

<400> SEQUENCE: 25
tccacctcta agcctcaaca c                                                  21

<210> SEQ ID NO 26
<211> LENGTH: 23
<212> TYPE: DNA
<213> ORGANISM: Artificial
<220> FEATURE:
<223> OTHER INFORMATION: Fig 3A: lane 1, Primer RNa

<400> SEQUENCE: 26
```

```
gcggatccat gaaggagacc gcc                                              23

<210> SEQ ID NO 27
<211> LENGTH: 56
<212> TYPE: DNA
<213> ORGANISM: Artificial
<220> FEATURE:
<223> OTHER INFORMATION: Figure 3A: Lane 2

<400> SEQUENCE: 27
gcggatccat gaaggagacc gccgccgcca agttcgagcg ccagcacatg gacagc        56

<210> SEQ ID NO 28
<211> LENGTH: 22
<212> TYPE: DNA
<213> ORGANISM: Artificial
<220> FEATURE:
<223> OTHER INFORMATION: Figure 3A: Lane 3, RN1

<400> SEQUENCE: 28
catagatctt tagctgtcca tg                                               22

<210> SEQ ID NO 29
<211> LENGTH: 28
<212> TYPE: DNA
<213> ORGANISM: Artificial
<220> FEATURE:
<223> OTHER INFORMATION: Fig 3A: lane 4, Primer

<400> SEQUENCE: 29
ccagatctat gagctcctcc aactactg                                         28

<210> SEQ ID NO 30
<211> LENGTH: 63
<212> TYPE: DNA
<213> ORGANISM: Artificial
<220> FEATURE:
<223> OTHER INFORMATION: Fig 3A: lanes 2/5, RNII

<400> SEQUENCE: 30
taaagatcta tgagcacctc cgccgccagc tcctccaact actgcaacca gatgatgaag    60
tct                                                                   63

<210> SEQ ID NO 31
<211> LENGTH: 21
<212> TYPE: DNA
<213> ORGANISM: Artificial
<220> FEATURE:
<223> OTHER INFORMATION: Fig 3A: lane 6, RN2

<400> SEQUENCE: 31
tcaggttcct agacttcatc a                                                21

<210> SEQ ID NO 32
<211> LENGTH: 59
<212> TYPE: DNA
<213> ORGANISM: Artificial
<220> FEATURE:
<223> OTHER INFORMATION: Fig 3A, lanes 5/7, RNIII

<400> SEQUENCE: 32
aggaacctga ccaaggacag gtgcaagcca gtcaacacct tcgtccacga gagcctggc     59

<210> SEQ ID NO 33
```

-continued

```
<210> SEQ ID NO 33
<211> LENGTH: 19
<212> TYPE: DNA
<213> ORGANISM: Artificial
<220> FEATURE:
<223> OTHER INFORMATION: Fig 3A: lane 8, RN3

<400> SEQUENCE: 33
ctggacatcg gccaggctc                                                  19

<210> SEQ ID NO 34
<211> LENGTH: 48
<212> TYPE: DNA
<213> ORGANISM: Artificial
<220> FEATURE:
<223> OTHER INFORMATION: Fig 3A, lanes 7/9, RN IV

<400> SEQUENCE: 34
cgatgtccag gccgtctgca gccagaagaa cgtggcctgc aagaacgg                  48

<210> SEQ ID NO 35
<211> LENGTH: 21
<212> TYPE: DNA
<213> ORGANISM: Artificial
<220> FEATURE:
<223> OTHER INFORMATION: Fig 3A: lane 10, RN 4

<400> SEQUENCE: 35
agttggtctg accgttcttg c                                               21

<210> SEQ ID NO 36
<211> LENGTH: 60
<212> TYPE: DNA
<213> ORGANISM: Artificial
<220> FEATURE:
<223> OTHER INFORMATION: Fig 3A: lanes 9/11, RN V

<400> SEQUENCE: 36
tcagaccaac tgctaccagt cctacagcac catgtccatc accgactgcc gcgagaccgg     60

<210> SEQ ID NO 37
<211> LENGTH: 19
<212> TYPE: DNA
<213> ORGANISM: Artificial
<220> FEATURE:
<223> OTHER INFORMATION: Fig 3A: lane 12, RN5

<400> SEQUENCE: 37
cttgctggag ccggtctcg                                                  19

<210> SEQ ID NO 38
<211> LENGTH: 55
<212> TYPE: DNA
<213> ORGANISM: Artificial
<220> FEATURE:
<223> OTHER INFORMATION: Fig 3A: lanes 11/13, RN VI

<400> SEQUENCE: 38
ctccagcaag taccctaact gcgcctacaa gaccacccag gccaacaagc acatc          55

<210> SEQ ID NO 39
<211> LENGTH: 21
<212> TYPE: DNA
<213> ORGANISM: Artificial
<220> FEATURE:
<223> OTHER INFORMATION: Fig 3A: lane 14, RN 6

<400> SEQUENCE: 39
```
caggcaacaa tgatgtgctt g                                          21

<210> SEQ ID NO 40
<211> LENGTH: 24
<212> TYPE: DNA
<213> ORGANISM: Artificial
<220> FEATURE:
<223> OTHER INFORMATION: Fig 3A: lane 15, Primer RN-b

<400> SEQUENCE: 40
cgggatcctt tagacggagg cgtc                                       24

<210> SEQ ID NO 41
<211> LENGTH: 66
<212> TYPE: DNA
<213> ORGANISM: Artificial
<220> FEATURE:
<223> OTHER INFORMATION: Fig 3A: lanes 13/16, RN VII

<400> SEQUENCE: 41
attgttgcct gcgagggtaa cccttacgtg cctgtccact tcgacgcctc cgtctaaagg    60
atcccg                                                           66

<210> SEQ ID NO 42
<211> LENGTH: 23
<212> TYPE: DNA
<213> ORGANISM: Artificial
<220> FEATURE:
<223> OTHER INFORMATION: Fig 3B: lane 1, PCR Primer RNa

<400> SEQUENCE: 42
gcggatccat gaaggagacc gcc                                        23

<210> SEQ ID NO 43
<211> LENGTH: 56
<212> TYPE: DNA
<213> ORGANISM: Artificial
<220> FEATURE:
<223> OTHER INFORMATION: Fig 3B, lane 2, RN I

<400> SEQUENCE: 43
gcggatccat gaaggagacc gccgccgcca agttcgagcg ccagcacatg gacagc        56

<210> SEQ ID NO 44
<211> LENGTH: 18
<212> TYPE: DNA
<213> ORGANISM: Artificial
<220> FEATURE:
<223> OTHER INFORMATION: Fig 3B, lane 3, RN 7

<400> SEQUENCE: 44
ccaccgccgc tgtccatg                                              18

<210> SEQ ID NO 45
<211> LENGTH: 57
<212> TYPE: DNA
<213> ORGANISM: Artificial
<220> FEATURE:
<223> OTHER INFORMATION: Fig 3B: lanes 2/4, RN VIII

<400> SEQUENCE: 45
ggcggtggcg gttccggtgg cggtggcagc ggcggcggtg gtagcaagat cttcggg       57

<210> SEQ ID NO 46

```
<211> LENGTH: 18
<212> TYPE: DNA
<213> ORGANISM: Artificial
<220> FEATURE:
<223> OTHER INFORMATION: Fig 3B: lane 5, RN c

<400> SEQUENCE: 46
cccgaagatc ttgctacc                                              18

<210> SEQ ID NO 47
<211> LENGTH: 45
<212> TYPE: DNA
<213> ORGANISM: Artificial
<220> FEATURE:
<223> OTHER INFORMATION: Fig 4, lane 1

<400> SEQUENCE: 47
aaagagacag cagccgcaaa gtttgagcgt cagcatatgg atagt                45

<210> SEQ ID NO 48
<211> LENGTH: 32
<212> TYPE: PRT
<213> ORGANISM: Artificial
<220> FEATURE:
<223> OTHER INFORMATION: Fig 4A: lane 2
<220> FEATURE:
<221> NAME/KEY: Xaa
<222> LOCATION: (17)..(17)
<223> OTHER INFORMATION: Xaa corresponds to an ochre stop codon (UAA)

<400> SEQUENCE: 48

Met Lys Glu Thr Ala Ala Ala Lys Phe Glu Arg Gln His Met Asp Ser
1               5                   10                  15

Xaa Gly Gly Gly Gly Ser Gly Gly Gly Ser Gly Gly Gly Gly Ser
            20                  25                  30

<210> SEQ ID NO 49
<211> LENGTH: 63
<212> TYPE: DNA
<213> ORGANISM: Artificial
<220> FEATURE:
<223> OTHER INFORMATION: Fig 4A: lane 3

<400> SEQUENCE: 49
ggatccatga aggagaccgc cgccgccaag ttcgagcgcc agcacatgga cagctaaaga    60
tct                                                                 63

<210> SEQ ID NO 50
<211> LENGTH: 106
<212> TYPE: DNA
<213> ORGANISM: Artificial
<220> FEATURE:
<223> OTHER INFORMATION: Fig 4A: lane 4

<400> SEQUENCE: 50
ggatccatga aggagaccgc cgccgccaag ttcgagcgcc agcacatgga cagcggcggt    60
ggcggttccg gtggcggtgg cagcggcggc ggtggtagca agatct                  106

<210> SEQ ID NO 51
<211> LENGTH: 330
<212> TYPE: DNA
<213> ORGANISM: Artificial
<220> FEATURE:
<223> OTHER INFORMATION: Fig 4B: lane 1

<400> SEQUENCE: 51
```

-continued

```
agcaccagtg ctgccagttc ttccaactac tgtaaccaga tgatgaagtc tagaaacttg    60
accaaggaca gatgtaagcc agttaacaca tttgtccacg agagtttggc tgatgtccaa   120
gccgtctgca gtcagaaaaa cgttgcatgc aagaacggtc aaacgaactg ttaccagagt   180
tacagcacca tgtccatcac tgactgtcgt gagacaggct cgagcaagta tcctaattgt   240
gcttacaaga ccacacaggc gaacaaacac atcattgttg cttgtgaagg taacccttac   300
gttcctgtcc actttgacgc cagtgtttaa                                    330
```

<210> SEQ ID NO 52
<211> LENGTH: 132
<212> TYPE: PRT
<213> ORGANISM: Artificial
<220> FEATURE:
<223> OTHER INFORMATION: Fig 4B: lane 2

<400> SEQUENCE: 52

```
Met Ser Thr Ser Ala Ala Ser Ser Asn Tyr Cys Asn Gln Met Met
1               5                   10                  15

Lys Ser Arg Asn Leu Thr Lys Asp Arg Cys Lys Pro Val Asn Thr Phe
            20                  25                  30

Val His Glu Ser Leu Ala Asp Val Gln Ala Val Cys Ser Gln Lys Asn
        35                  40                  45

Val Ala Cys Lys Asn Gly Gln Thr Asn Cys Tyr Gln Ser Tyr Ser Thr
    50                  55                  60

Met Ser Ile Thr Asp Cys Arg Glu Thr Gly Ser Ser Lys Tyr Pro Asn
65                  70                  75                  80

Cys Ala Tyr Lys Thr Thr Gln Ala Asn Thr Asp Cys Arg Glu Thr Gly
                85                  90                  95

Ser Ser Lys Tyr Pro Asn Cys Ala Tyr Lys Thr Thr Gln Ala Asn Lys
            100                 105                 110

His Ile Ile Val Ala Cys Glu Gly Asn Pro Tyr Val Pro Val His Phe
        115                 120                 125

Asp Ala Ser Val
    130
```

<210> SEQ ID NO 53
<211> LENGTH: 346
<212> TYPE: DNA
<213> ORGANISM: Artificial
<220> FEATURE:
<223> OTHER INFORMATION: Fig 4B, lane 3

<400> SEQUENCE: 53

```
agatctatga gcacctccgc cgccagctcc tccaactact gcaaccagat gatgaagtct    60
aggaacctga ccaaggacag gtgcaagcca gtcaacacct cgtccacga gagcctggcc   120 gatgtccagg ccgtctgcag ccagaagaac gtggcctgca agaacggtca gaccaactgc   180
taccagtcct acagcaccat gtccatcacc gactgccgcg agaccggctc cagcaagtac   240
cctaactgcg cctacaagac cacccaggcc aacaagcaca tcattgttgc ctgcgagggt   300
aacccttacg tgcctgtcca cttcgacgcc tccgtctaaa ggatcc                  346
```

<210> SEQ ID NO 54
<211> LENGTH: 331
<212> TYPE: DNA
<213> ORGANISM: Artificial
<220> FEATURE:
<223> OTHER INFORMATION: Fig 4B, lane 4

<400> SEQUENCE: 54

| agatctatga gctcctccaa ctactgcaac cagatgatga agtctaggaa cctgaccaag | 60 |
| gacaggtgca agccagtcaa cacctccgtc cacgagagcc tggccgatgt ccaggccgtc | 120 |
| tgcagccaga gaacgtggc ctgcaagaac ggtcagacca actgctacca gtcctacagc | 180 |
| accatgtcca tcaccgactg ccgcgagacc ggctccagca agtaccctaa ctgcgcctac | 240 |
| aagaccacac aggccaacaa gcacatcatt gttgcctgcg agggtaaccc ttacgtgcct | 300 |
| gtccacttcg acgcctccgt ctaaaggatc c | 331 |

<210> SEQ ID NO 55
<211> LENGTH: 163
<212> TYPE: DNA
<213> ORGANISM: Artificial
<220> FEATURE:
<223> OTHER INFORMATION: Fig 4C i

<400> SEQUENCE: 55

| tctagatctt aacatgaaga atgttttagt aaggtcagct gcgcgagctc tgcttggcgg | 60 |
| cggtgggcgg agctactacc gccagctctc aacggcggcg atcgtggaac agagacacca | 120 |
| gcacggtggc ggcgcgtttg aagcttcca cttaagcgga tcc | 163 |

<210> SEQ ID NO 56
<211> LENGTH: 198
<212> TYPE: DNA
<213> ORGANISM: Artificial
<220> FEATURE:
<223> OTHER INFORMATION: Fig 4C ii

<400> SEQUENCE: 56

| atgaagaatg ttttagtaag gtcagctgcg cgagctctgc ttggcggcgg tgggcggagc | 60 |
| tactaccgcc agctctcaac ggcggcgatc gtggaacaga gaccagca cggtggcggc | 120 |
| gcgtttggaa gcttccactt aagaaggatg aaggagaccg ccgccgccaa gttcgagcgc | 180 |
| cagcacatgg acagctaa | 198 |

<210> SEQ ID NO 57
<211> LENGTH: 270
<212> TYPE: DNA
<213> ORGANISM: Artificial
<220> FEATURE:
<223> OTHER INFORMATION: Fig 4c iii

<400> SEQUENCE: 57

| atgaagaatg ttttagtaag gtcagctgcg cgagctctgc ttggcggcgg tgggcggagc | 60 |
| tactaccgcc agctctcaac ggcggcgatc gtggaacaga gaccagca cggtggcggc | 120 |
| gcgtttggaa gcttccactt aagaaggatg aaggagaccg ccgccgccaa gttcgagcgc | 180 |
| cagcacatgg acagcggcgg tgcggttcc ggtggcggtg gcagcggcgg cggtggtagc | 240 |
| gggatccccg ggtacggtca gtcccttatg | 270 |

<210> SEQ ID NO 58
<211> LENGTH: 465
<212> TYPE: DNA
<213> ORGANISM: Artificial
<220> FEATURE:
<223> OTHER INFORMATION: Fig 4C iv

<400> SEQUENCE: 58

-continued

```
atgaagaatg ttttagtaag gtcagctgcg cgagctctgc ttggcggcgg tgggcggagc      60
tactaccgcc agctctcaac ggcggcgatc gtggaacaga gacaccagca cggtggcggc     120
gcgtttggaa gcttccactt aagaaggatg agctcctcca actactgcaa ccagatgatg     180
aagtctagga acctgaccaa ggacaggtgc aagccagtca cacctccgt ccacgagagc      240 ctggccgatg tccaggccgt ctgcagccag aagaacgtgg cctgcaagaa cggtcagacc     300
aactgctacc agtcctacag caccatgtcc atcaccgact gccgcgagac cggctccagc     360
aagtacccta actgcgccta caagaccaca caggccaaca agcacatcat tgttgcctgc     420
gagggtaacc cttacgtgcc tgtccacttc gacgcctccg tctaa                    465
```

<210> SEQ ID NO 59
<211> LENGTH: 715
<212> TYPE: DNA
<213> ORGANISM: Artificial
<220> FEATURE:
<223> OTHER INFORMATION: Fig 4C v

<400> SEQUENCE: 59

```
atgcagatct tcgtgaaaac cttgaccggc aagaccatca ctctcgaggt cgagagcagc      60
gacaccatcg acaatgtcaa ggccaagatc aagacaaag aaggtatcat tcttcctcac      120
tcaatctgga ttcttctctt tagcttttg aaattcagat tcttatcat ttacttgttt       180 ctcctttaag gaatccctcc ggatcagcag agattgatct tcgccggaaa gcagctcgaa     240
gatggccgta ctttggctga ctacaacatc cagaaaggta cgaaatcatc cgaatccttc     300
tgttgatcat ttcgatgatc tgattgtata aactctaatg gattgttatc atttgtaaac     360
agaatctaca cttcatcttg tgttgaggct tagaggtgga tccagctcca actactgcaa     420
ccagatgatg aagtctagga acctgaccaa ggacaggtgc aagccagtca cacctccgt      480 ccacgagagc ctggccgatg tccaggccgt ctgcagccag aagaacgtgg cctgcaagaa     540
cggtcagacc aactgctacc agtcctacag caccatgtcc atcaccgact gccgcgagac     600
cggctccagc aagtacccta actgcgccta caagaccaca caggccaaca agcacatcat    660
tgttgcctgc gagggtaacc cttacgtgcc tgtccacttc gacgcctccg tctaa         715
```

<210> SEQ ID NO 60
<211> LENGTH: 27
<212> TYPE: DNA
<213> ORGANISM: Artificial
<220> FEATURE:
<223> OTHER INFORMATION: T PCR Primer Sprot F

<400> SEQUENCE: 60

```
ggtggatcca gctccaacta ctgcaac                                         27
```

<210> SEQ ID NO 61
<211> LENGTH: 24
<212> TYPE: DNA
<213> ORGANISM: Artificial
<220> FEATURE:
<223> OTHER INFORMATION: TPCR Primer Sprot R

<400> SEQUENCE: 61

```
cgggatcctt agacggaggc gtcg                                            24
```

<210> SEQ ID NO 62
<211> LENGTH: 31
<212> TYPE: DNA
<213> ORGANISM: Artificial

```
<220> FEATURE:
<223> OTHER INFORMATION: TPCR Primer Sprot MI1

<400> SEQUENCE: 62
gtccttaaga aggatgagct cctccaacta c                              31

<210> SEQ ID NO 63
<211> LENGTH: 24
<212> TYPE: DNA
<213> ORGANISM: Artificial
<220> FEATURE:
<223> OTHER INFORMATION: TPCR Primer Sprot MI2

<400> SEQUENCE: 63
cgggatcctt agacggaggc gtcg                                      24

<210> SEQ ID NO 64
<211> LENGTH: 29
<212> TYPE: DNA
<213> ORGANISM: Artificial
<220> FEATURE:
<223> OTHER INFORMATION: TPCR Primer Spep MI1

<400> SEQUENCE: 64
gtccttaaga aggatgaagg agaccgccg                                 29

<210> SEQ ID NO 65
<211> LENGTH: 27
<212> TYPE: DNA
<213> ORGANISM: Artificial
<220> FEATURE:
<223> OTHER INFORMATION: TPCR Primer Spep MI2

<400> SEQUENCE: 65
tcgggatcct tagctgtcca tgtgctg                                   27

<210> SEQ ID NO 66
<211> LENGTH: 27
<212> TYPE: DNA
<213> ORGANISM: Artificial
<220> FEATURE:
<223> OTHER INFORMATION: TPCR Primer Spep GMI2

<400> SEQUENCE: 66
tcgggatcct cattgtttgc ctccctg                                   27

<210> SEQ ID NO 67
<211> LENGTH: 32
<212> TYPE: DNA
<213> ORGANISM: Artificial
<220> FEATURE:
<223> OTHER INFORMATION: TPCR Primer AOX3MI1

<400> SEQUENCE: 67
tgctctagat cttaacatga agaatgtttt ag                             32

<210> SEQ ID NO 68
<211> LENGTH: 30
<212> TYPE: DNA
<213> ORGANISM: Artificial
<220> FEATURE:
<223> OTHER INFORMATION: TPCR Primer AOX3MI2

<400> SEQUENCE: 68
tcggatccgc ttaagtggaa gcttccaaac                                30
```